United States Patent [19]

Onoue et al.

[11] Patent Number: 5,143,910

[45] Date of Patent: Sep. 1, 1992

[54] PIPERAZINIOCEPHALOSPORINS

[75] Inventors: Hiroshi Onoue, Nara; Toshiro Konoike; Hiroyuki Ishitobi, both of Osaka, all of Japan

[73] Assignee: Shionogi & Co., Ltd., Osaka, Japan

[21] Appl. No.: 571,411

[22] Filed: Aug. 23, 1990

[30] Foreign Application Priority Data

Sep. 7, 1989 [JP] Japan .................. 1-232631

[51] Int. Cl.$^5$ ................ C07D 501/38; A61K 31/545
[52] U.S. Cl. ..................... 514/201; 514/202; 514/206; 540/221; 540/222
[58] Field of Search ............ 540/225, 222, 221; 514/201, 202

[56] References Cited

U.S. PATENT DOCUMENTS

| | | | |
|---|---|---|---|
| 4,782,155 | 11/1988 | Nakagawa et al. | 546/26 |
| 4,785,090 | 11/1988 | Tsuruoka et al. | 540/229 |
| 4,880,795 | 11/1989 | Angerbauer et al. | 540/222 |

FOREIGN PATENT DOCUMENTS

| | | |
|---|---|---|
| 52240 | 7/1986 | Australia . |
| 53295 | 8/1986 | Australia . |
| 188255 | 7/1986 | European Pat. Off. . |
| 0272827 | 6/1988 | European Pat. Off. . |
| 52-85187 | 7/1977 | Japan . |
| 61-17589 | 1/1986 | Japan . |
| 61-194088 | 8/1986 | Japan . |
| 62-5961 | 1/1987 | Japan . |
| 62-30786 | 2/1987 | Japan . |
| 62-209082 | 9/1987 | Japan . |
| 62-228085 | 10/1987 | Japan . |
| 63-10793 | 1/1988 | Japan . |
| 63-185985 | 8/1988 | Japan . |

Primary Examiner—Nicholas S. Rizzo
Attorney, Agent, or Firm—Birch, Stewart, Kolasch & Birch

[57] ABSTRACT

Antibacterial hydroxyarylpiperazinocephalosporins of the formula:

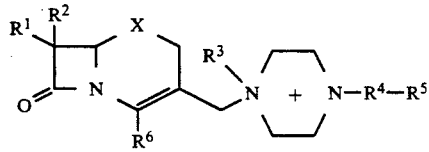

wherein $R^1$ is amino or acylamino; $R^2$ is H or methoxy; $R^3$ is alkyl; $R^4$ is $-(P-C-Q)_n-$, where P and Q each are H, alkyl or OH, or P and Q combine to form oxo, and n is 0 or 4; $R^5$ is substituted or unsubstituted hydroxyaryl; $R^6$ has a negative charge and is COO, or an anion in combination with an optionally protected carboxy; and X is O, S or S→O; an antibacterial preparation containing the same; a method for killing bacteria and preventing or treating bacterial infection by using the same; and syntheses of the cephalosporins are provided.

19 Claims, No Drawings

PIPERAZINIOCEPHALOSPORINS

The present invention relates to antibacterial cephalosporin compounds. This invention provides antibacterial cephalosporins, a bactericidal method and a treatment of bacterial infection using the compounds, and a process for the synthesis of the compounds. More specifically, it relates to hydroxyarylated piperaziniocephalosporins (I) represented by the following formula; the compounds possess superior antibacterial activity( e.g., against pseudomonal bacteria):

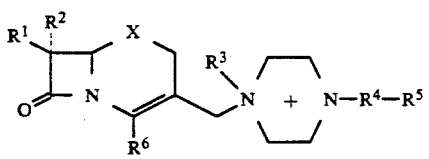

(wherein,
$R^1$ is amino or acylamino;
$R^2$ is hydrogen or methoxy;
$R^3$ is alkyl;
$R^4$ is $-(P-C-Q)_n-$
where P and Q each are hydrogen, alkyl, hydroxy, or P and Q combine to form oxo, and n is an integer 0 to 4;
$R^5$ is an optionally substituted hydroxyaryl or hydroxyheterocyclyl;
$R^6$ has a negative charge and is $COO^{31}$ or an anion $(Y^-)$ in combination with an optionally protected carboxy; and
X is O, S, or S→O.

The groups of compound (I) are explained as follows:
When $R^1$ is acylamino, its acyl can belong to the series of aliphatic, alicyclic, or aromatic carboxylic acyl including those forming amido side chains of natural or synthetic penicillins and cephalosporins. Followings are representative acyls:
$R^{10}R^{11}-CO-$ (wherein, $R^{10}$ is hydrogen, or aliphatic, aromatic, heterocyclic, or alicyclic group);
$R^{11}$ is a single bond, $-R^{12}CH_2-$ ($R^{12}$ is a single bond, oxygen, sulfur, or imino), $>CH-R^{13}$ (including stereoisomeric D and L isomers in which D is usually preferable); $>C=R^{14}$ (including geometric isomers E and Z in which Z is usually preferable), or the like divalent group.

Preferably, $R^{10}$ is 1C to 8C aliphatic group (e.g., optionally substituted alkyl, alkenyl, alkinyl), monocyclic or polycyclic aromatic group (e.g., optionally substituted phenyl, naphthyl, indanyl), monocyclic or polycyclic heterocyclic group (optionally substituted, five- or six-membered hetero ring group having up to 4 nitrogens, oxygen, and/or sulfur as hetero atom), mono- or poly-cyclic alicyclic group (optionally substituted 4 to 8 membered cycloalkyl optionally having 1 or 2 double bonds), a group constituting 2C to 9C carbonic acyl (e.g., alkoxy, alkylthio, aralkoxy, aralkylthio, aryloxy, arylthio, heterocyclyoxy), or the like.

Representative $R^{13}$ includes optionally protected carboxy, cyano, hydroxy, amino, sulfo, mercapto, and the like.

When $R^{13}$ is protected, the protecting group can be that aiming to avoid adverse change during the synthesis (e.g., ester, amide, halide, ether, anhydride) or that aiming to alter its physiological or pharmaceutical characteristics. Representatives of the former are, when $R^{13}$ is hydroxy, sulfhydryl, amino, or the like, 1C to 8C alkyl (e.g., methyl, ethyl, isopropyl, butyl, t-butyl, cyclopentyl), monocyclic hetero ring group (e.g., tetrahydropyranyl, tetrahydrofuranyl), 2C to 9C alkenyl (forming enol ether, enamine), 3C to 10C alkykl and/or alkoxysilyl or stannyl (e.g., trimethylsilyl, triethylsilyl, dimethyl-t-butylsilyl, trimethylstannyl, dimethylmethoxysilyl), 7C to 15C aralkyl (e.g., trityl, substituted diphenylmethyl, phenacyl), 1C to 10C acyl (e.g., alkanoyl, alkenoyl, aroyl, carbonic acyl); when $R^{13}$ is carboxy, sulfo, etc., an ester forming group (e.g., 1C to 8C alkyl, 7C to 20C aralkyl, 5C to 12C aryl), amide forming group (e.g., amino, 1C to 8C alkylamino, 2C to 8C dialkylhydrazinyl), salt forming group (e.g., alkali metal, alkaline earth metal, 2C to 10C amine), or the like removable without adverse effect on other part of the molecule. Representatives of the latter are; a group removable in vivo (e.g., salt, pharmaceutically active ester or amide, as given below) when $R^{13}$ is carboxy or sulfo; sulfo, carbamoyl, sulfamoyl, 2C to 9C carbalkoxy, 8C to 15C carbaralkoxy, 1C to 8C alkanoyl, 8C to 15C aralkanoyl, 7C to 15C aroyl, monocyclic heterocyclocarbonyl, cyano, or the like when $R^{13}$ is hydroxy; 1C to 8C alkylsulfonyl, monocyclic arylsulfonyl, 1C to 8C alkyloxoimidazolidinylcarbonyl, dioxopiperazinylcarbonyl, alkylureidocarbonyl, thioureidocarbonyl, or the like when $R^{13}$ is amino; and the like.

Representative $R^{14}$ includes oxo, thioxo, imino, hydroxyimino, optionally substituted and optionally unsaturated alkoxyimino, aralkoxyimino, aryloxyimino, alkylidene, and the like. Preferable are 1C to 8C saturated or unsaturated, straight or cyclic group and the like when $R^{14}$ is oxyimino or alkylidene and mono- or polycyclic carbo- or hetero-cyclic group when it is aryloxyimino. Each can have a substituent (e.g., carboxy, esterified or amidated carboxy, hydroxy, 1C to 8C alkyl, 1C to 8C alkoxy). $R^{10}$ to $R^{14}$ can further have a substituent as given below. The acyl remaining in the objective antibacterial has preferably 20 or less carbon atoms.

This cephalosporin has arylpiperaziniomethyl at position 3. This piperazinio ring has a group $R^4R^5$ at position 4.

$R^4$ is $-(P-C-Q)_n-$ (where, P, Q each is hydrogen, lower alkyl, hydroxy, or combined P and Q are oxo, and n is 0 to 4). Preferably, it is carbonyl or a divalent group of the formula $-R^{12}CH_2-$ ($R^{12}$ is as above). Representative are alkylene, carbonyl, oxoalkylene, and the like.

$R^5$ is hydroxyaryl (e.g., phenyl, naphthyl), hydroxylated hetero ring group (e.g., pyridine ring, pyran ring). Said hydroxyaryl, hydroxy hetero ring group can be substituted. Representative substituents are amino, hydroxy, alkali metaloxy, alkaline earth metal oxy, 1C to 8C alkoxy, 1C to 8C acyloxy, 3C to 9C silyloxy, 7C to 15C aralkoxy, 2C to 9C alkoxycarbonyloxy, halogen, nitro, cyano, carboxy, carbamoyl, 2C to 9C alkoxycarbonyl, 8C to 15C aralkoxycarbonyl, 1C to 8C alkyl, 2C to 9C alkenyl, monocyclic heterocyclyl thio, and the like. The hydroxy of the hydroxyaryl or hydroxyheterocyclyl $R^5$ may be protected. This hydroxy-protecting group includes an easily removable ester forming group [carboxylic acyl (e.g., 1C to 10C alkanoyl as formyl, acetyl, propionyl, pivaloyl, octyl and monocyclic aroyl as benzoyl, toluoyl, xyloyl), 2C to 10C carbonic acyl (e.g., 2C to 8C alkoxycarbonyl, benzyloxycarbonyl, p-methoxybenzyloxycarbonyl, p-tolylmethoxycarbonyl, nitrobenzyloxycarbonyl, allyloxycarbonyl)] and easily removable ether-forming group [2C to 8C alkyl (e.g., t-butyl, tetrahydropyranyl, tetrahydrofuryl, methoxymethyl, methoxyethoxymethyl), 3C to 18C hydrocarbylsilyl (e.g., trimethylsilyl, triethylsilyl, dimethylphenylsilyl, diphenyl-t-butylsilyl, triphenylsilyl, dimethyl-t-pentylsilyl), or 7C to 19C reactive aralkyl (e.g., benzyl, p-methoxybenzyl, triphenylmethyl)]. Representative $R^5$ are vicinal dihydroxyphenyl or vicinal dihydroxypyridyl optionally substituted by methyl, chloro, or lower alkoxy. The compounds (I) having these are stronger antibacterials against, e.g., *Pseudomonas aeruginosa, Serratia marcescens, Morgania morganii, Enterobacter cloacae, Clostridium freundii.*

The protected carboxy in $R^5$ is a modified carboxy group for protection or for medical use.

The protected carboxy in $R^6$ are known in the field of penicillin and cephalosporin chemistry as those protected by a group capable of being introduced and removed without adversely effecting other parts of the molecule and can have up to 19C. The carboxy-protecting groups can be used for reactions or medicines (i.e., that forming medical salts or pharmaceutically active esters).

Representative are the carboxy protecting groups for reaction purposes including an ester forming group, 1C to 8C alkyl (e.g., methyl, methoxymethyl, ethyl, ethoxymethyl, iodoethyl, propyl, isopropyl, butyl, isobutyl, ethoxyethyl, methylthioethyl, methylsulfonylethyl, trichloroethyl, t-butyl), 3C to 8C alkenyl (e.g., propenyl, allyl, prenyl, hexenyl, phenylpropenyl, dimethylhexenyl), 7C to 19C aralkyl (e.g., benzyl, methylbenzyl, dimethylbenzyl, methoxybenzyl, ethoxybenzyl, nitrobenzyl, aminobenzyl, diphenylmethyl, phenethyl, trityl, di-t-butylhydroxybenzyl, phthalidyl, phenacyl), 6C to 12C aryl (e.g., phenyl, tolyl, xylyl, diisopropylphenyl, trichlorophenyl, pentachlorophenyl, indanyl), 1C to 12C N-substituted amino (ester group with e.g., actone oxime, acetophenone oxime, acetaldoxime, N-hydroxysuccinimide, N-hydroxyphthalimide), 3C to 12C hydrocarbyl silyl (e.g., trimethylsilyl, dimethylmethoxysilyl, t-butyldimethylsilyl), 3C to 12C hydrocarbylstannyl (e.g., trimethylstannyl), and the like protecting groups. The protecting group may optionally be substituted by a group as given below. As the carboxy protecting group is absent in the objective product, its structure is unimportant so far as the protection is effective. A wide range of equivalent groups (e.g., amide, anhydride with carbonic or carboxylic acid) are available.

The said medically modified carboxy in $R^6$ includes a carboxy salt group, pharmaceutically active ester protected carboxy, or the like.

Preferably, the carboxy salt group in $R^6$ can be ammonia or a pharmaceutically available ion-forming light metal of Group I to III, Period 2 to 4 in the periodic table and known in the field of penicillins and cephalosporins. Representative light metals include lithium, sodium, potassium, magnesium, calcium, aluminum, or the like. Ammonium salts are suitable for synthesis or storage. Representative are 1C to 12C alkylammonio (e.g., trimethylammonio, triethylammonio, methylmorpholinio) and 4C to 9C aromatic base (e.g., pyridinio, collidinio, picolinio, quinolinio, dimethylanilinio) salt group.

Pharmaceutically active ester protected carboxy in $R^6$ is a group capable of forming a carboxy ester showing antibacterial activity in oral and parenteral administration. Representative are the groups forming 2C to 15C 1-oxygen substituted alkyl {alkanoyloxyalkyl (e.g., acetoxymethyl, pivaloyloxymethyl, cyclohexylacetoxyethyl), 3C to 15C alkoxycarbonyloxyalkyl (e.g., ethoxycarbonyloxyethyl, isopropoxycarbonyloxyethyl, cyclohexyloxycarbonyloxyethyl), 2C to 8C alkoxyalkyl (e.g., methoxymethyl), 4C to 8C 2-oxacycloalkyl (e.g., tetrahydropyranyl), or the like}, 8C to 12C substituted aralkyl (e.g., phenacyl, phthalydyl), 6C to 12C aryl (e.g., phenyl, indanyl), or 2C to 12C alkenyl (e.g., allyl, (2-oxo-1,3-dioxol-4-yl)methyl) esters groups.

The counter-ion $Y^-$ of the piperazinio can be an organic or inorganic anion. Representative are chloride, bromide, iodide, sulfate, carboxylate, and sulfonate, and the like anions.

The said groups $R^1$ to $R^6$ may optionally have a substituent as follows. Said carbon numbers include that of the substituents.

$R^1$ to $R^5$ having carboxy as substituent can form a derivative (e.g., salt, ester) as given above in relation to $R^6$.

$R^1$ to $R^6$ having phenol as substituent can form a salt (e.g., with an organic base, alkali metal, alkaline earth metal). $R^1$ to $R^6$ having hydroxy or phenol can optionally be protected by a hydroxy protecting group introducible and removable without adversely changing other parts of the molecule and have from 1 to 20 carbon atoms. Representative of such substituents are optionally further substituted 1C to 8C alkyl (e.g., t-butyl, methoxymethyl, methoxyethoxymethyl, trichloroethyl, tetrahydropyranyl), 7C to 20C aralkyl (e.g., benzyl, diphenylmethyl, trityl, methoxybenzyl, nitrobenzyl, methylbenzyl), 3C to 15C trialkylsilyl, 3C to 15C trialkylstannyl, 1C to 8C alkanoyl (e.g., formyl, acetyl, chloroacetyl, trichloroacetyl, trifluoroacetyl), 7C to 15C aroyl (e.g. benzoyl, nitrobenzoyl), 2C to 12C alkoxycarbonyl (in which alkyl part is, e.g., methyl, ethyl, propyl, cyclopropylethyl, isopropyl, butyl, hexyl, isobutyl, trichloroethyl, pyridylmethyl, cyclopentyl, cyclohexyl), 8C to 15C aralkoxycarbonyl (in which aralkyl part is, e.g., benzyl, diphenylmethyl, nitrobenzyl), 3C to 10C dibasic acid acyl (e.g., succinyl, phthaloyl), halosulfonyl, 0C to 10C phosphoric acyl (e.g., dialkoxyphosphoryl, phenyldichlorophosphoryl), and other hydroxyprotecting groups.

$R^1$ to $R^6$ having amino can form a salt with inorganic or organic acid and can be protected to avoid adverse changes during a reaction. This amino-protection is made with a 1C to 20C amino-protecting group introducible and removable without adversely changing other parts of the molecule. Representative are optionally further substituted 1C to 8C alkyl (e.g., t-butyl, methoxymethyl, methoxyethoxymethyl, trichloroethyl, tetrahydropyranyl), 7C to 20C aralkyl (e.g., benzyl, diphenylmethyl, trityl, methoxybenzyl, nitrobenzyl, methylbenzyl), 6C to 12C arylthio (e.g., nitrophenylthio), 1C to 8C alkyldene, 7C to 14C aralkylidene (e.g., optionally substituted benzylidene), acyl [1C to 8C alkanoyl (e.g., formyl, acetyl, chloroacetyl, trichloroacetyl, trifluoroacetyl), 7C to 15C aroyl (e.g., benzoyl, nitrobenzoyl), 2C to 12C alkoxycarbonyl (alkyl part is, e.g., methyl, ethyl, propyl, cyclopropylethyl, isopropyl, butyl, hexyl, isobutyl, trichloroethyl, pyridylmethyl, cyclopentyl, cyclohexyl), 8C to 15C aralkoxycarbonyl (its aralkyl part is e.g., benzyl, tolylmethyl, xylylmethyl, diphenylmethyl, nitrobenzyl), 3C to 10C dibasic acid acyl (e.g., succinyl, phthaloyl), halosulfonyl, 0C to 10C phosphoric acyl (e.g., dialkoxyphosphoryl, phenyldichlorophosphoryl), or the like], 3C to 15C trialkylsilyl, 3C to 15C trialkylstannyl and the like amino-protecting groups.

Scope of Groups

The alkyl part of the said groups is straight, branched or cyclic alkyl. Representatives are 1C to 12C alkyl (e.g., methyl, ethyl, propyl, isopropyl, cyclopropyl, butyl, isobutyl, t-butyl, cyclobutyl, cyclopropylmethyl, pentyl, isopentyl, neopentyl, cyclopentyl, cyclopropylethyl, hexyl, cyclohexyl, cyclopentylmethyl, heptyl, cycloheptyl, cyclopentylethyl, cyclohexylmethyl, octyl, cyclooctyl, cyclohexylethyl, nonyl, dodecyl). These may be unsaturated or may be substituted as given below.

The aralkyl part is a combination of said alkyl and aryl below. Representative is 7C to 14C aralkyl (e.g., benzyl, phenethyl, phenylpropyl, phenylisopropyl, diphenylmethyl, methoxydiphenylmethyl, naphthylmethyl, furylmethyl, thienylpropyl, oxazolylmethyl, thiazolylmethyl, imidazolylmethyl, triazolylmethyl, pyridylmethyl, indolylmethyl, benzoimidazolylethyl, benzothiazolylmethyl, quinolylmethyl). These may optionally be substituted as given below.

The said acyl part has the structure as above pertaining to $R^1$. Representative are up to 14C acyl, for example, carboxylic acyl (e.g., straight, branched or cyclic alkanoyl, monocyclic or dicyclic aroyl, aralkanoyl, or arylalkenoyl optionally having a hetero atom), sulfonic acyl (e.g., alkylsulfonyl, arylsulfonyl), carbonic acyl (e.g., cabamoyl, carbalkoxy, carbaralkoxy), sulfo, and the like. These may optionally be substituted as given below.

The aryl part is monocyclic or bicyclic, 5 to 6-membered carbocyclic or heterocyclic aryl. This heterocyclic group may have oxygen, nitrogen, or sulfur as hetero atom. Representative are 1C to 10C aryl, e.g., heteroaryl (e.g., furyl, thienyl, pyrrolyl, oxazolyl, thiazolyl, imidazolyl, oxadiazolyl, thiadiazolyl, triazolyl, thiatriazolyl, tetrazolyl, pyridyl, pyranyl, indolyl, benzofuryl, benzothienyl, benzoimidazolyl, benzothiazolyl, benzopyrazinyl, quinolyl, pyridopyridyl) and carbocyclic aryl (e.g., phenyl, naphthyl, indenyl, indanyl, tetralinyl). These may optionally be substituted as given below.

Representative substituents which may be attached to said groups include a carbon function (e.g., straight, branched or cyclic alkyl, alkenyl, alkinyl, aralkyl, aryl, heterocyclyl, carboxylic acyl, carbamoyl, carboxy, protecting carboxy, cyano); a nitrogen function (e.g., amino, acylamino, guanidyl, ureido, alkylamino, dialkylamino, isothiocyano, isocyano, nitro, nitroso); an oxygen function (e.g., hydroxy, alkoxy, aryloxy, heterocyclyoxy, cyanato, oxo, carboxylic acyloxy, sulfonic acyloxy, phosphoric acyloxy); a sulfur function (e.g., mercapto, alkylthio, alkylsulfonyl, arylthio, arylsulfonyl, heterocyclythio, heterocyclylsulfonyl, acylthio, thioxo, sulfo, sulfamoyl); halogen (e.g., fluoro, chloro, bromo, iodo, pseudohalogeno); silyl (e.g., trialkylsilyl, dialkylalkoxysilyl); stannyl (e.g., trialkylstannyl); and the like.

Illustration of Compounds (I)

Typical free compounds (I) include the followings:

(1) A betaine of the following formula and its sulfoxides.

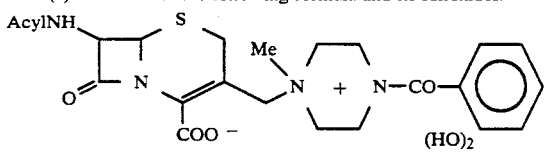

| Acyl | position of (OH)₂ |
| --- | --- |
| 1) Aroyl | |
| benzoyl | 2,3 |
| p-methylbenzoyl | 3,4 |
| 2,6-dimethoxybenzoyl | 2,3 |
| 5-phenyl-3-methyl-4-isoxazolylcarbonyl | 3,4 |
| 2) Alkanoyl | |
| formyl | 2,3 |
| acetyl | 2,3 |
| acetyl | 3,4 |
| phenoxyacetyl | 3,4 |
| difluoromethylthioacetyl | 2,3 |
| difluoromethylthioacetyl | 3,4 |
| cyanomethylthioacetyl | 2,3 |
| cyanomethylthioacetyl | 3,4 |
| aminoadipoyl | 2,3 |
| aminoadipoyl | 3,4 |
| 3) Aralkanoyl | |
| phenylacetyl | 2,3 |
| phenylacetyl | 3,4 |
| mandeloyl | 3,4 |
| α-(2-thienyl)acetyl | 3,4 |
| tetrazolylacetyl | 3,4 |
| phenylmalonyl | 2,3 |
| phenylmalonyl | 3,4 |
| α-sulfophenylacetyl | 3,4 |
| cyanoacetyl | 2,3 |
| cyanoacetyl | 3,4 |
| α-aminophenylacetyl | 3,4 |
| p-hydroxyphenyl-α-aminoacetyl | 3,4 |
| α-carbamoylamino-p-hydroxyphenylacetyl | 3,4 |

-continued

| | |
|---|---|
| α-(4-ethyl-2,3-dioxopiperazinylcarbonylamino)phenylacetyl | 3,4 |
| 4) Thiazolyloximes | |
| 2-(2-amino-4-thiazolyl)-2-hydroxyiminoacetyl | 2,3 |
| 2-(2-amino-4-thiazolyl)-2-hydroxyiminoacetyl | 3,4 |
| 2-(2-amino-4-thiazolyl)-2-methoxyiminoacetyl | 2,3 |
| 2-(2-amino-4-thiazolyl)-2-methoxyiminoacetyl | 3,4 |
| 2-(2-amino-4-thiazolyl)-2-carboxymethoxyiminoacetyl | 3,4 |
| 2-(2-amino-4-thiazolyl)-2-(1-carboxy-1-methylethoxyimino)acetyl | 2,3 |
| 2-(2-amino-4-thiazolyl)-2-(1-carboxy-1-methylethoxyimino)acetyl | 3,4 |
| 2-(5-amino-1,2,4-thiadiazol-3-yl)-2-methoxyiminoacetyl | 2,3 |
| 2-(5-amino-1,2,4-thiadiazol-3-yl)-2-methoxyiminoacetyl | 3,4 |
| 2-(5-amino-1,2,4-thiadiazol-3-yl)-2-hydroxyiminoacetyl | 3,4 |
| 5) carboxyacryl | |
| 2-(2-amino-4-thiazolyl)-4-carboxy-2-butenoyl | 2,3 |
| 2-(2-amino-4-thiazolyl)-4-carboxy-2-butenoyl | 3,4 |
| 2-(2-amino-4-thiazolyl)-5-carboxy-2-pentenoyl | 2,3 |
| 2-(2-amino-4-thiazolyl)-6-carboxy-2-hexenoyl | 3,4 |
| 2-(5-amino-1,2,4-thiadiazol-3-yl)-6-carboxy-2-hexenoyl | 3,4 |
| 6) Carbonic acyl | |
| t-butoxycarbonyl | 2,3 |
| t-butoxycarbonyl | 3,4 |
| trichloroethoxycarbonyl | 3,4 |
| benzyloxycarbonyl | 2,3 |
| benzyloxycarbonyl | 3,4 |
| methylbenzyloxycarbonyl | 2,3 |

(2) A betaine of the following formula and its sulfoxides.

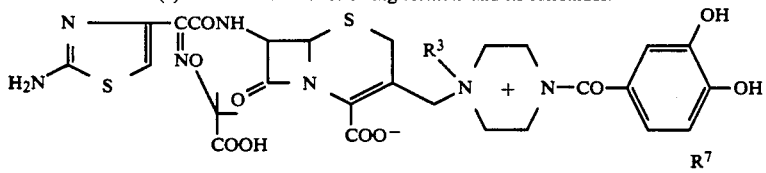

In the above formula ($R^7$=H), $R^3$ is, e.g., methyl, ethyl, propyl, butyl, isobutyl.

In the above formula ($R^3$=methyl), $R^7$ is, e.g., fluoro, chloro, methyl, ethyl, isopropyl, hydroxy, methoxy, acetoxy.

Related Technology

Among known cephalosporins having 3-ammoniomethyl, Japanese Pat. Publ. Kokai SHO 61-194088 describes piperaziniomethyl, but none has 3-hydroxy(-homo or hetero)aroylpiperaziniomethyl. The hydroxyaroyl is a specific anti-Pseudomonal structure in beta-lactam antibacterials (e.g., Pat. Publ. Kokai SHO 52-85187). However, it is unknown as the substituent on 3-piperziniomethyl.

Use and Effect

The compounds (I) show potent antibacterial activity against aerobic and anaerobic Gram-positive (e.g., Staphylococcusaureus) and Gram-negative bacteria (e.g., Escherichia coli). Especially, the representative cathecolated piperazinio compounds (I) are superior in, e.g., the antibacterial activity against Pseudomonas aeruginosa, Serratio marcescens, Morgaia morganii, Enterobacter cloacae, Clostridium freundii, or the like various Gram negative bacteria, the high blood level, the rapid excretion.

For example, a representative 3-(4-(3,4-dihydroxybenzoyl)piperazinio)methyl-7β-(2-(2-aminothiazol-4-yl)-2-(1-carboxy-1-methylethoxy)iminoacetamido)-3-cephem-4-carboxylate has superior characters as medicines as exemplified by its high antibacterial activity against Pseudomonas aeruginosa SR 24 MIC=0.1γ/ml, $ED_{50}$(mouse)=1.41 mg/kg, Pseudomonas aeruginosa SR 5018 MIC=0.05γ/ml, Pseudomonas aeruginosa SR 4967, $ED_{50}$(mouse)=4.91 mg/kg, Serratia marcescens A 13880 $ED_{50}$(mouse)=0.28 mg/kg, and clinically isolated Morgania morganii, Enterobacter cloacae, and Clostridium freundii; high urinary and bile juice recovery during 2 hours after subcutaneous injection (20 mg/kg) reaching totally 70.4%; and high maximum plasma level of 53.7 mg/ml.

Further, Compound (I) having halogen (e.g., 2-chloro, 5-chloro, 6-chloro, 2,5-dichloro) on the 3,4-dihydroxybenzoyl ring of $R^4R^5$ is superior to the corresponding compound without the chloroatom, e.g., in its antibacterial activity, metabolism, excretion, side effects.

Compound (I) of this invention is superior to known cephalosporin as having similar structure or activity as follows:

(1) vs Other anti-pseudomonal compounds

Compound (I) has superior anti-pseudomonal activity to the known anti-pseudomonal cephalosporins.

3-Pyridiniomethyl compounds

Compound (I) has superior anti-pseudomonal activity to 3-pyridiniomethyl compounds.

For example, MIC of said representative compound is 500 times more potent against ofloxacin resistant Pseudomonas aeruginosa SR 5018 as compared with 25γ/ml of the reference ceftazidime.

3-Alkylpyridiniothiomethyl compounds

Compound (I) has superior anti-pseudomonal activity to the corresponding compounds having 3-pyridiniothiomethyl.

For example, MIC of said representative compound is 63 to 250 times more potent against Pseudomonas aeruginosa SR 24 as compared with 25γ/ml of the reference 3-(1-methylpyridinio-4-yl)thiomethyl compound (Japanese Pat. Publ. Kokai SHO 62-5961), 12.5γ/ml of the reference 3-(1-carbamoylmethylpiridinio-4 -ylthiomethyl compound (Japanese Pat. Publ. Kokai SHO 62-228085), and 6.3γ/ml of the reference 3-(1-carbamoylmethyl-2,3-trimethylenepyridinio-4-ylthiomethyl compound (Japanese Pat. Publ. Kokai SHO 61-17589).

(2) vs. Other catechol compounds

Compound (I) has superior anti-pseudomonal activity to other dihydroxyaryl cephalosporins.

3-Pyridiniomethyl compounds

Compound (I) has superior anti-pseudomonal activity to 3-pyridiniomethyl compounds.

For example, MIC of said representative compound is 8 times more potent against *Pseudomonas aeruginosa* SR 5018 as compared with 0.4γ/ml of the reference BO-1341: 3-(6,7-dihydroxyisoquinolinio)methyl-7β-(2-(2-aminothiazol-4-yl)-2-(1-carboxy-1-methylethoxyimino)acetamido)-3-cephem-4-carboxylate (Japanese Pat. Publ. Kokai SHO 63-10793).

3-Dihydroxybenzyl compounds

Compound (I) has superior anti-pseudomonal activity to the corresponding compounds having 3-hydroxybenzyl.

For example, $ED_{50}$ of said representative compound is 2.4 times more potent against *Pseudomonas aeruginosa* SR 24 as compared with 3.4 mg/kg of the reference 3-(3,4-dihydroxybenzyl) compound (Japanese Pat. Publ. Kokai SHO 62-209082).

Thiadiazolylthiomethyl compounds

Compound (I) has superior anti-pseudomonal activity to the compounds having 3-dihydroxyphenylheterocyclylthiomethyl.

For example, $ED_{50}$ of said representative compound is 11.6 times more potent against *Pseudomonas aeruginosa* SR 24 as compared with 16.3 mg/kg of the reference 3-(dihydroxyphenylthiadiazolylthio)methyl compound (Japanese Pat. Publ. Kokai SHO 63-185985).

Dihydroxybenzoylaminomethyl compounds

Compound (I) has superior anti-pseudomonal activity to the compounds having 3-vic. dihydroxybenzoylaminomethyl.

(3) vs. Structurally similar compounds

Ammoniomethyl compounds

Compound (I) has superior anti-pseudomonal activity to the compounds having 3-ammoniomethyl.

For example, MIC of said representative compound is 126 times more potent against *Pseudomonas aeruginosa* SR 5018 as compared with 6.3 γ/ml of the reference E-1040: 3-(4-carbamoylquinuclidinio)methyl-7β-(2-(5-amino-1,2,4-thiadiazol-4-yl)-2-methoxyiminoacetamido)-3-cephem-4-carboxylate (Japanese Pat. Publ. Kokai SHO 62-30786).

Use

Utilizing said antibacterial activity of compound (I), this invention provides the following uses (1) to (4).

(1) A bactericidal or bacteriostatic method by bringing Compound (I) to contact with a sensitive bacteria.

(2) A method for killing bacteria, inhibiting or preventing bacterial growth, disinfecting, preventing putrefaction of a material, by applying an effective amount of Compound (I) to a portion of material where sensitive bacteria are growing or supposed to grow.

(3) A method for preventing or treating human or animal infection caused by sensitive bacteria and for promoting growth by administering compound (I) singly or in admixture with other medicals. This invention, for example, provides a method for treating or preventing human or veterinary bacterial infections caused by sensitive bacteria (e.g., respiratory tract infection, nasopharyngitis, rhinitis, empyema, tonsillitis, pharyngitis, bronchitis, pneumonia, pneumonitis, urinary tract infection, pyelonephritis, dermatitis, ulceration, pustulosis, abscess, ear infection, digestive tract infection, osteomyelitis, septicemia, wound and soft tissue infection, post operative infection, gynecological infection) by administering an effective amount of the said compound (I) at an effective daily dose of 0.1 to 6 g (injection), 0.4 to 4 g (orally), or 0.01 to 10 mg (topically).

(4) A use of compound (I) as a starting material for producing other antibacterials and a material for sensitivity test of bacteria.

Composition

This invention also provides an antibacterial pharmaceutical formulation containing said compound (I). This is provided in various dosage forms (e.g., solution, dispersion, or suspension) (I) solely or containing 0.01 to 99% of compound in admixture with a conventional carrier for solid or liquid compositions.

The composition of compound (I) as a free acid or light metal salt is available by formulating in a conventional manner, if required with a carrier, to give injection (e.g., ampoule, vial, solution, or suspension, for intravenous, intramuscular, drip, or subcutaneous injection), external medicine, topical medicine (e.g., ear-, nose-, or eye-lotion, ointment, emulsion, spray, suppository), oral medicine (with a enteral adsorption-promoting agent), or the like. The pharmaceuitcally active ester (I) is used as injection, external, topical medicine, enteral medicine, or the like.

The carrier is that available pharmacologically and pharmaceutically and inert to the compound (I). Among others representative carriers include a solvent (e.g., alcohol, buffer, methyl oleate, water), buffer, dispersing agent, solubilizing agent, stabilizing agent (e.g., methyl or ethyl p-hydroxybenzoate, sorbic acid), absorption promoter (e.g., glycerin mono- or di-octanoate), antioxidant, aromatic substance, analgesic, emulsifying agent, an agent for controlling side effects or enhancing the activity (e.g., absorption or excretion controlling agent, enzymatic decomposition preventing agent, β-lactamase inhibitor, other antibacterial) or the like.

The pharmaceutical preparation can be prepared conventionally.

Production

This invention provides some methods for producing compound (I). For example, the objective compounds can be prepared as follows from a known substance.

Amido group formation

The objective compound (I) or its derivatives can be prepared by reacting amine (II) or its reactive derivative with carboxylic acid (III) or its reactive derivative in a conventional manner.

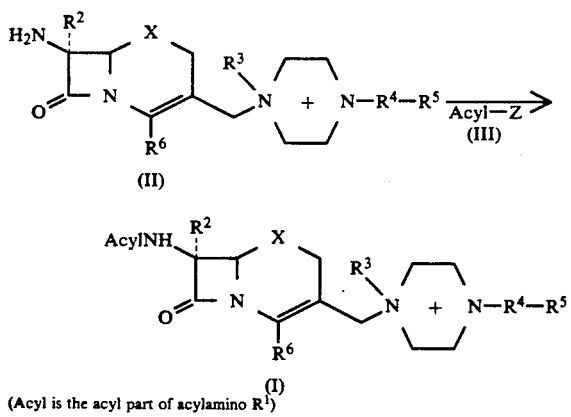

(Acyl is the acyl part of acylamino $R^1$)

The said reactive derivative of amine (II) is that in which the 7-amino is activated with 1C to 10C groups, for example, silyl (e.g. trimethylsilyl, triethylsilyl, methoxydimethylsilyl, t-butyldimethylsilyl), stannyl (e.g., trimethylstannyl), alkylene (a group forming enamine of said amino with, e.g., alkanal, acetone, acetylacetone, acetoacetate, acetacetanilide, acetoacetonitrile, cyclopentanedione, acetylbutyrolactone), alkylidene (e.g., 1-haloalkylidine, 1-haloaralkylidene, 1-alkoxyalkylidene, 1-alkoxyaralkylidene, 1-alkoxy-1-phenoxyalkylidene, alkylidene, aralkylidene), acid (as a salt with, e.g., mineral acid, carboxylic acid, sulfonic acid), easily removable acyl (e.g., alkanoyl), or the like and that in which other functional group of the molecule is protected.

Carboxylic acid (III:Z=OH) is reacted in the presence of a condensing reagent [carbodiimide (e.g., N,N'-diethylcarbodiimide, N,N'-dicyclohexylcarbodiimide), carbonyl compound (e.g., carbonyldiimidazole), isoxazolinium salt, acylamino compound (e.g. 2-ethoxy-1-ethoxycarbonyl-1,2-dihydroquinoline), or the like].

The reaction is preferably carried out in a solvent having no reactive hydrogen with 1 to 2 mole of carboxylic acid (III) and 1 to 2 mole of the condensing reagent per mole of amine (II).

Typical reactive derivative (III) is acid anhydride {symmetric acid anhydride, mixed acid anhydride [e.g., mixed acid anhydride with mineral acid (e.g., phosphoric acid, sulfuric acid, carbonic acid half ester), organic acid (e.g., alkanoic acid, aralkanoic acid, sulfonic acid)], intramolecular anhydride (e.g., ketene, isocyanate), acid halide (i.e., mixed anhydride with hydrogen halide)}, acid halide, reactive ester [enol ester (e.g., vinyl or isopropenyl ester), aryl ester (e.g., phenyl, halophenyl, or nitrophenyl ester), heterocyclyl ester (e.g., pyridyl or benzotriazolyl ester), ester with an N-hydroxy compound ester with diacylhydroxylamine (e.g., N-hydroxysuccinimidoyl ester, N-hydroxyphthalimidoyl ester), thiol ester (e.g., aralkylthiol ester, heterocyclylthiol ester), or the like], reactive amide [e.g., aromatic amide (e.g., amide with imidazole, triazole, 2-ethoxy-1,2-dihydroquinoline), diacylanilide], and other reactive derivatives. These reactive derivatives are used in the presence of an acid scavenger [inorganic base (oxide, hydroxide, carbonate, bicarbonate, of e.g., alkali metal, alkaline earth metal), organic base (e.g., tertiary amine, aromatic base), oxirane (e.g., alkylene oxide, aralkylene oxide), pyridinium salt (e.g., tripyridiniotriazine trichloride), adsorbent (e.g., Celite), or the like]. This reaction is preferably carried out in a solvent having no reactive hydrogen with 1 to 2 mole of carboxylic acid (III) reactive derivative and 0 to 2 mole of the acid scavenger per mole of amine (II). An acid halide and enzymatically reactive ester can be used in an aqueous solvent.

Amide cleavage

The amido group of compound (I:$R^1$=acylamino) can be cleaved easily to give the corresponding 7-compound (I:$R^1$=amino). The amide was treated in a conventional solvent (e.g., halohydrocarbon) with phosphorus pentachloride at −20° to 50° C. for 1 to 5 hours to give iminochloride. The imino chloride was converted by treatment with alcohol (e.g., methanol, ethanol, propanol) at −60° to −20° C. for 10 to 90 minutes into imino ether, and subsequently to the amino by acid hydrolysis. The yield may be improved by adding a reagent for preventing side reaction (e.g., secondary amine).

Introduction of piperazinio

In a conventional manner, 3-Z-substituted methyl compound (II: preferably, Z is mineral acid acyl (e.g., phosphoric, sulfuric, or carbonic half acyl)-oxy, organic acyl (e.g., alkanoyl, aralkanoyl, sulfonyl)-oxy, halo (chloro, bromo, iodo), or the like) is treated

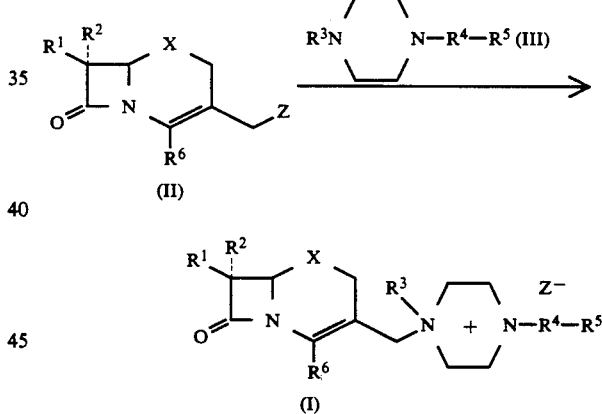

with the corresponding piperazine (III) or its reactive derivative (preferably 1 to 3 equivalents) to give the corresponding 3-piperaziniiomethyl compound (I). The leaving group Z (e.g., chloro) may be replaced by higher reactive one (e.g., iodo) prior to the reaction. The reaction completes at 0°~50° C. for 20 minutes to 1 week.

Introduction of $R^4$-$R^5$

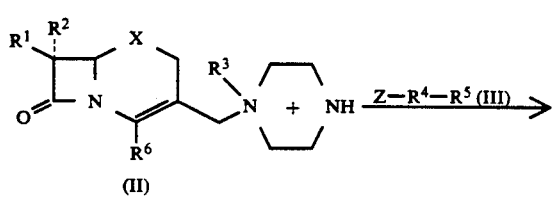

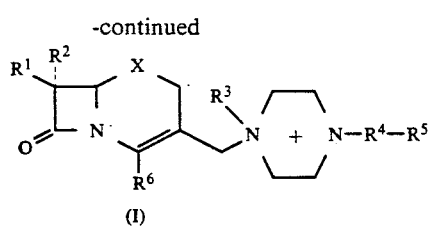

(I)

The conventional treatment of 3-(unsubstituted piperazinio)methyl compound (II) with the correspond $R^5R^4Z$ (III:Z is as defined above: preferably 1 to 2 Eq.) gives the corresponding 3-(substituted piperazinio)-methyl compound (I). The reaction completes at 0° to 50° C. for 20 minutes to 12 hours.

Protection of carboxy

An ester (I) can be produced by esterifying a compound having free carboxy or its reactive derivative (e.g., salt, anhydride, halide, reactive ester), for example, in an inert solvent at 0° C. to 50° C. by a conventional method as follows:

a) A reaction of the alcohol with carboxylic acid (I) or its reactive derivative in the presence of an acid scavenger or condensing reagent as given under the section of amide formation.

b) A reaction of e.g., halide, sulfonate, with carboxylic acid (I) or its reactive derivative in the presence of an acid scavenger.

c) A reaction of a diazo compound with the carboxylic acid (I).

Deprotection of protected carboxy

A compound (I) having a carboxy-protecting group can be deprotected conventionally in an inert solvent to give carboxylic acid (I). This deprotection includes, for example, the followings:

a) A highly reactive ester groups as carboxy-protecting group can be deprotected by contacting it to acid, base, buffer solution, ion-exchange resin, or the like in an inert solvent. Some insufficiently reactive esters may be deprotected after activation conventionally to easily be deprotected (for trichloroethyl ester with metal and acid; for p-nitrobenzyl ester by hydrogenation, or with dithionate or metal and acid; and for phenacyl ester by irradiation);

b) An aralkyl ester group as a carboxy-protecting groups can be deprotected by a conventional hydrogenation in the presence of a catalyst (e.g., palladium, platinum, nickel);

c) A t-alkyl, cyclopropylmethyl, 2-alkenyl, aralkyl, sulfonylethyl, etc., ester group as carboxy-protecting groups may be deprotected by treating, for example, with a mineral acid, Lewis acid (e.g., aluminum chloride, tin tetrachloride, titanium tetrachloride), sulfonic acid (e.g., benzenesulfonic acid, methanesulfonic acid, trifluoromethanesulfonic acid), strong carboxylic acid (e.g., trifluoroacetic acid), or the like, if required in the presence of a cation scavenger (e.g. anisole, benzenethiol);

d) A 2-alkenyl ester group as carboxy-protecting group can be deprotected by the action of triarylphosphine-palladium complex;

e) A phenacyl, 2-alkenyl, hydroxyaralkyl, or the like ester group as carboxy-protecting group can be deprotected by the action of a base or nucleophilic reagent; or A free acid compound (I) is treated with a base or its salt of weak acid to give the corresponding salt (I). For example, it is prepared by neutralizing a free acid with a base (e.g., hydroxide, carbonate, hydrogen carbonate, of light metal) or by treating with light metal lower carboxylate (e.g., sodium acetate, sodium lactate, sodium 2-ethylhexanoate) in a polar organic solvent (e.g., alcohol, ketone, ester) and then diluting with a less polar solvent to separate the salt, or lyophilizing a salt solution to leave the salt.

The reaction completes usually 1 to 10 minutes at under 50° C., but the mixture may be kept longer if no adverse side reaction occurs.

Oxidation to sulfoxide

Compound (I) having a sulfide group in its molecule can be oxidized conventionally, for example, by the following oxidizing method to give the corresponding sulfoxide (I).

Thus, sulfide (I) is treated with following oxidizing reagent (e.g., ozone, inorganic peracid, percarboxlic acid, persulfonic acid, or the like industrially available peracid, hydrogen, peroxide, perboric acid, urea peroxide, nickel peroxide, sodium peroxide, preferably 1 to 2 equivalents), if required in the presence of reaction accelerator (a salt of acid of VII group atom in the Periodic Table, e.g. tungustate, phosphoric acid, polyphosphoric acid, phosphate ester, alkanoic acid), preferably in an inert solvent (e.g., halohydrocarbon, ester, water) preferably at −10° to 35° C. for 1 to 20 hours to give the sulfoxide. When the starting compound has a double bond at position 2, it migrates to position 3.

Reduction of sulfoxide

Compound (I) having sulfinyl in the molecule can be reduced conventionally to given the corresponding sulfide (I). Thus, sulfoxide (I) is treated with 2 to 5 molar equivalents of a reducing reagent (e.g., trivalent phosphous compound, iodide, stannous compound) in an inert solvent (e.g., dimethylformammide, dichloromethane, dioxane) at −50° to 50° C. for 20 minutes to 10 hours to give the corresponding sulfide (I).

Protection of hydroxy

A hydroxy group (including a salt of phenolic hydroxy) can be protected by introducing an acyl or ether type protecting group by a conventional reaction of protecting reagent (e.g., halide, anhydride, reactive ester, of the acyl or ether-type protecting group), if required in the presence of an acid scavenger (e.g., aromatic base, alkali metal hydroxide, alkaline earth metal hydroxide, alkali metal carbonate, alkaline earth metal carbonate, alkali metal bicarbonate, alkaline earth metal bicarbonate).

Deprotection of protected hydroxy

A protected hydroxy group can be deprotected by a method as given under the title of deprotection of carboxy-protecting group. For example, by the action of, e.g., a strong carboxylic acid, Lewis acid, if required in the presence of cation scavenger to cleave ether bond, by the action of, e.g., acid or base to hydrolyze an ester group. A protecting group of a phenolic hydroxy can easily be deprotected.

Introduction of amino-protecting group

A conventional protecting group can be introduced on the amino group of compound (I) under a condition as follows:

a) Alkoxycarbonyl, aralkoxycarbonyl, alkanoyl group, and the like are introduced by treating with the corresponding halide or anhydride (preferably 1 to 5 Eq.) in the presence of an acid scavenger at −30° to 50° C.

b) Alkoxycarbonyl, aralkoxycarbonyl, alkanoyl, arylsulfenyl, aralkyl, trialkylsilyl, trialkylstannyl, and the like by the action of a halide of the group (1 to 5 Eq.) in the presence of an acid scavenger (1 to 10 Eq.) in a solvent at −30° to 100° C. for 1 to 10 hours.

c) Trialkylsilyl by a conventional action of a reactive derivative [e.g., disilazanes, acetamides, halides (e.g., hexamethyldisilazane, bistrimethylsilylacetamide, trimethylsilyl chloride).

d) By a conventional action of acyl azide (e.g., tosyl azide) to give azido as protected amino.

Deprotection of protected amino group

Compound (I) having protected amino group in the molecule can be deprotected, for example, as follows:

a) Alkoxycarbonylamino (e.g. t-butoxycarbonylamino), or the like protected amino group by the action of a strong acid (e.g., trifluoracetic acid, trifluoromethanesulfonic acid), Lewis acid (e.g., aluminum chloride, stannic chloride, titanium chloride, zinc chloride), or other acid, if required in the presence of a cation scavenger (e.g. anisole, benzenethiol).

b) Aralkoxycarbonylamino (e.g., carbobenzoxyamino, methylcarbobenzoxyamino, diphenymethoxycarbonylamino) or the like protected amino group by the action of the said Lewis acid and carbonium cation scavenger or by hydrogen (e.g., catalytic hydrogenation using palladium or nickel catalyst).

c) lower alkanoylamino (e.g., formyl, acetyl, chloroacetyl), Schiff base group (e.g., ethylideneamino, propylideneamino, optionally substituted benzylideneamino), aralkylamino (e.g., optionally substituted tritylamino), arylthioamino (e.g., phenylsulfenylamino), silylamino or stannylamino (e.g., trimethylstannylamino, trimethylsilylamino), or the like protected amino group by the action of acid (e.g., hydrochloric acid, sulfuric acid, methanesulfonic acid), or the like.

d) Methods specific for each protecting group (for example, thiourea or N-alkyldithiocarbamate for haloacetylamino; hydrazine for dibasic acid acylamino; phosphorus pentachloride and alkanol for acylamino; reduction or hydrogenation for azido; etc.

Other productions

These group and its introduction and elimination can be done, e.g., as follows, by applying convention methods.

When the 7-side chain is 2-aminothiazolyl-2-substituted oxyiminoacetoamido, the compound (I) can be prepared conventionally by the ring closure of the aminothiazole ring from the corresponding haloacetoacetoamido compound and thiourea, or oxime formation from the corresponding 2-oxoacetoamido compound and hydroxylamine.

Reaction conditions

The said syntheses each is usually carried out at −50° C. to 100° C. especially −20° C. to 50° C., for 10 minutes to 10 hours. If the product is stable in the reaction mixture, the mixture can be kept for longer time. If required, these are carried out under dry condition or inert gas atmosphere in a solvent with stirring, or the like conventional condition.

Reaction solvent

The reaction solvent for this invention can be a hydrocarbon (e.g., pentane, hexane, octane, benzene, toluene, xylene), halohydrocarbon (e.g., dichloromethane, chloroform, carbon tetrachloride, dichloroethane, trichloroethane, chlorobenzene), ether (e.g., diethyl ether, methyl isobutyl ether, dioxane, tetrahydrofuran), ketone (e.g., acetone, methyl ethyl ketone, cyclohexanone), ester (e.g., ethyl acetate, isobutyl acetate, methyl benzoate), nitrohydrocarbon (e.g., nitromethane, nitrobenzene), nitrile (e.g., acetonitril, benzonitrile), amide (e.g., formamide, acetamide, dimethylformamide, dimethylacetamide, hexamethylphosphorotriamide), sulfoxide (e.g., dimethyl sulfoxide), carboxylic acid (e.g., formic acid, acetic acid, propionic acid), organic base (e.g., diethylamine, triethylamine, pyridine, picoline, collidine, quinoline), alcohol (e.g., methanol, ethanol, propanol, hexanol, octanol, benzyl alcohol), water, or the like industrial solvent or a mixture.

Work up

The objective products can be recovered from the reaction mixture after removing contaminants (e.g., unreacted starting material, by-products, solvents) by a conventional method (e.g., extracting, evaporating, washing, concentrating, precipitating, filtrating, drying) and purified by a combination of usual work up (e.g., adsorbing, eluting, distilling, precipitating, separating, chromatographying).

Abbreviations

| | | |
|---|---|---|
| Ac = acetyl. | BOC = t-butoxycarbonyl. | tBu = t-butyl. |
| BH = diphenylmethyl. | Me = methyl. | MO(column X) = X is O & $R^2$ is MeO. |
| PH = phenyl ring. | PMB = p-methoxybenzyl. | An = acetone. |
| Ani = anisole. | DCM = dichloromethane. | DMA = dimethylacetamide. |
| DMF = dimethylformamide. | TFA = trifluoroacetic acid. | |
| $ED_{50}$ = 50% effective dose. | MIC = minimal inhibitory concentration | |

G = phenylacetoamido.
FMOX = difluoromethylthioacetamido.
CTX = syn-2-(2-amino-4-thiazolyl)-2-methoxyiminoacetoamido.
CAZ = syn-2-(2-amino-4-thiazolyl)-2-amino-4-thiazolyl)-2-(1-carboxy-1-methylethoxyimino)acetamido.
ENL = syn-2-(2-amino-4-thiazolyl)-1-(1-carboxyvinyloxyimino)acetamido.
BOCCTX = syn-2-(2-t-butoxycarbonylamino-4-thiazolyl)-2-methoxyimino)acetamido.
BOCCAZtBu = syn-2-(2-t-butoxycarbonylamino-4-thiazolyl)-2-(1-t-butoxycarbonyl-1-methylethoxyimino)acetamido.

BOCCAZBH=syn-2-(2-t-butoxycarbonylamino-4-thiazolyl)-2-(1-diphenylmethoxycarbonyl-1-methylethoxyimino)acetamido.

BOCENLtBu=syn-2-(2-t-butoxycarbonylamino-4-thiazolyl)-2-(1-t-butoxycarbonylvinyloxyimino)acetoamido.

Examples

The following examples illustrate the embodiment of this invention.

The physical constants of the products are summarized in tables, where IR data show the wave number $\nu$ in $cm^{-1}$, NMR data show chemical shift $\delta$ in ppm and coupling constants J in Hz. In NMR data when a signal splitts, each chemical shifts are shown dividing with comma.

In the Examples, "part" shows amount parts by weight of and "equivalents" shows mole number per the starting $\beta$-lactam.

For work up of neutral products, usual reaction mixture is, if required, after diluting with a solvent, or water, etc., extracted, washed, dried, and concentrated in vacuo to give the product. This is isolated, if desired after purification by silica gel chromatography, etc., by crystallization, precipitation, filtration, solidification, or the like conventional methods or its combination.

EXAMPLE

Amidation

According to the following scheme 7$\beta$-amino compound (2) (1 mole) is amidated with carboxylic acid corresponding to 7$\beta$ -side chain (3) or its reactive, e.g., in a following manner to give amid (1).

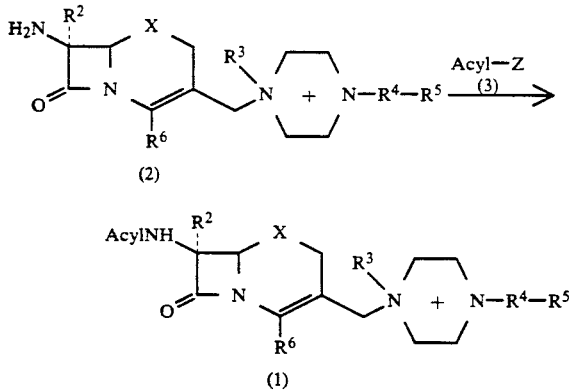

1) By stirring in a mixture of dichloromethane (10 Vol.), N,N-dicyclohexylcarbodiimide (1.1 Eq.), 2-ethoxy-1-ethoxycarbonyl-1,2-dihydroquinoline (1.1 Eq.), pyridine (1.5 Eq.) and carboxylic acid (3) (1.1 Eq.) at 0° C. to room temperature for 1 to 6 hours.

2) By stirring in a mixture of ethyl acetate (10 Vol.), di-2-pyridyl disulfide (1.1 Eq.), triphenylphosphine (1.1 Eq.), carboxylic acid (3) (1.1 Eq.) at 10° at 50° C. for 2 to 6 hours.

3) By stirring in a mixture of dichloromethane (3 Vol.), carboxylic acid (3) (1.1 Eq.), 1,3,5-tripyridiniotriazine trichloride (4 Eq.) at −10° to 10° C. for 1 to 5 hours.

4) By standing in a mixture of carbon tetrachloride (30 Vol.), N-methylmorpholine (1.5 Eq.), trisdiethylaminophosphine (1.1 Eq.). carboxylic acid (3) (1.1 Eq.) at −20° to 10° C. for 1 to 5 hours.

5) By stirring in a mixture of chloroform (10 Vol.), dimethoxyethane (10 Vol.), triethylamine (1.5 Eq.) and a mixed anhydride of carboxylic acid (3) and isobutoxyformic acid at −5° to 10° C. for 0.5 to 6 hours.

6) By heating in a refluxing mixture of ethyl acetate (10 Vol.), 1,2-dichloroethane (10 Vol.), N-methylmorpholine (1.5 Eq.) symmetric anhydride of carboxylic acid (3) (1.1 Eq.) for 10 minutes to 2 hours.

7) By stirring in a mixture of dichloroemthane (10 Vol.), pyridine (1.5 moles), and a mixed anhydride of carboxylic acid (3) and methanesulfonic acid warming from −70° C. to room temperature for 1 to.3 hours.

8) By stirring in a mixture of ethyl acetate (10 Vol.), a mixed anhydride of diethyl phosphate and carboxylic acid (3) (1.5 Eq.), and pyridine (1.5 Eq.) at 0° to 10° C. for 1 to 5 hours.

9) By stirring in a mixture of ethyl acetate (10 Vol.), dichloromethane (10 Vol.), N-methylmorpholine (1 Eq.), a mixed anhydride of carboxylic acid (3) and phosphoric acid dichloride at 0° C. to room temperature for 1 to 3 hours.

10) By stirring in a mixture of lutidine (1.5 Eq.), dichloromethane (10 Vol.), a mixed anhydride of phosphoric acid dimethylamide monochloride and carboxylic acid (3) (1.1 to 2 Eq.) at 0° to 30° C. for 1 to 4 hours.

11) By stirring in a mixture of dichloromethane (5 Vol.), trifluoroacetic acid anhydride (1.5 Eq.), pyridine (3 Eq.) and carboxylic acid (3) (1.5 Eq.) at 0° C. to room temperature for 1 to 5 hours.

12) By stirring in a mixture of dichloromethane (10 Vol.), diethyl phosphate bromide (1.2 Eq.), N-methylmorpholine (2.5 Eq.), and carboxylic acid (3) (1.2 Eq.) at 0° C. to room temperature to 1 to 3 hours.

13) When 4-carboxy of the compound (2) is free, this is dissolved in water (10 Vol.) containing aqueous sodium hydrogen carbonate (2.5 Eq.), mixed with carboxylic acid (3) chloride (1.1 Eq.) at −5° C. to room temperature for 30 minutes to 2 hours.

14) When 4-carboxy of compound (2) is free, this is treated with trimethylsilyl chloride and triethylamine (1.2 Eq. each) to O-silylate, with pyridine (4 Eq.) and carboxylic acid (3) chloride (1.1 Eq.) to N-acylate at −30° C. for 30 minutes to 2 hours, and then with acid to hydrolyze the silyl group.

15) By stirring in a solution of picoline (4 Eq.), carboxylic acid (3) chloride (1.2 Eq.), and dichloromethane (20 Vol.) at 0° to −30° C. for 30 minutes to 2 hours.

16) By stirring in a mixture of dimethylformamide (2 Vol.), ethyl acetate (10 Vol.), triethylamine (1.1 Eq.) and carboxylic acid (3) chloride (1.1 Eq.) at 0° to 20° C. for 30 minutes to 3 hours.

17) By stirring in a mixture of dichloromethane (30 Vol.), cyanuric chloride (1.1 Eq.), pyridine (4 Eq.), and carboxylic acid (3) (1.1 Eq.), at −30° to 10° C. for 5 minutes to 2 hours.

18) By stirring in a mixture of dichloromethane (3 Vol.), phosphorus oxychloride (1.1 Eq.), triethylamine (1.5 Eq.), and carboxylic acid (3) (1.1 Eq.) at −10° to 10° C. for 20 minutes to 2 hours.

19) Amine (1) is treated with trimethylsily chloride and an acid scavenger to give N-trimethylsilylated compound (2). By treating this with phosphorus oxychloride (1.5 Eq.), carboxylic acid (3) (1.2 Eq.), and dimethylaniline (4 Eq.) in dichloromethane (5 Vol.) at 0° C. to room temperature for 30 minutes to 2 hours.

20) By stirring in a mixture of dichloromethane (8 Vol.), thionyl chloride (1.5 Eq.), pyridine (2.5 Eq.) and carboxylic acid (3) (1.1 Eq.) at −30° to 0° C. for 1 to 5 hours.

21) By stirring in a mixture of chloroform (3 Vol.), toluene (1 Vol.), carboxylic acid (3) (1.1 Eq.), picoline (2 Eq.), and oxalyl chloride (1 Eq.) at −50° to 10° C. for 10 minutes to 2 hours.

22) By stirring in a mixture of dichloromethane (20 Vol.), pyridine (3 Eq.), carboxylic acid (3) 1-oxybenzotriazolyl ester (3 Eq.) at 10° to 50° C. for 5 to 30 hours.

23) By stirring in a mixture of dichloromethane (20 Vol.), 1-ethoxycarbonyl-2-ethoxy-1,2-dihydroquinonine (2.1 Eq.), N,N'-dicyclohexylcarbodiimide (2.5 Eq.), and carboxylic acid (3) (2 Eq.) at room temperature for 1 to 15 hours.

24) By stirring in a mixture of carboxylic acid (3) phthalimidoyl ester (2 Eq.) and dioxane (10 Vol.) at 10° to 50° C. for 2 to 8 hours.

(25) By stirring in a mixture of carboxylic acid (3) succinimidoyl ester (1.5 Eq.) and methyl isobutyl ketone (10 vol.) at 0° to 40° C. for 2 to 9 hours.

26) By stirring in a mixture of carbonyldiimidazole (1.1 Eq.), tetrahydrofuran (10 Vol.), dimethylacetamide (5 Vol.), and carboxylic acid (3) (1.1 Eq.) at 0° C. to room temperature for 1 to 5 hours.

27) By stirring in a mixture of dimethylformamide (5 Vol.), dimethylaniline (1.3 Eq.), carboxylic acid (3), the Vilsmeyer reagent of dimethylformamide (1.1 Eq.), and dimethylaniline (1.3 Eq.) at room temperature for 1 to 5 hours.

28) By heating in a mixture of dichloromethane (10 Vol.), dimethylformamide (5 Vol.), N,N-dicyclohexylcarbodiimide (1.1 Eq.), picoline (1.2 Eq.), and carboxylic acid (3) (1.1 Eq.), for 2 to 24 hours.

29) To a mixture of 7β-amino-3-[4-{3,4-bis(p-methoxybenzyloxy)benzoyl}-1-methylpiperazinio-1-yl]methyl-3-cephem-4-carboxylic acid p-methoxybenzyl ester chloride mono hydrochlonic acid salt. (2) (1.76 g: 2 mMol.) in dichloromethane (15 ml) at 0° C. are added N-methylmorpholin (0.21 ml: 1 Eq.), and 2-(2-t-butoxycarbonylamino-4-thiazolyl)-2-(1-t-butoxycarbonyl-1-methylethoxyimino)acetic acid (3) (1.12 g: 1.3 Eq.). The mixture is cooled to −40° C., mixed with phenyl dichlorophosphate (0.39 ml: 1.3 Eq.) and N-methylmorpholine (0.65 ml: 3 Eq.), and stirred at −40° C. to −20° C. for 30 minutes. The reaction mixture is diluted with ice water, washed with diluted hydrochloric acid and water, dried, and concentrated under reduced pressure. The residue is triturated in ether to give 7β-[2-(2-t-butoxycarbonylamino-4-thiazolyl)-2-(1-(1-t-butoxycarbonyl-1-methylethoxyimino)acetamido]-3-[4-{3,4-bis(p-methoxybenzyloxy)benzoyl}-1-methylpiperazinio-1-yl]methyl-3-cephem-4-carboxylic acid p-methoxybenzyl ester chloride (1) (1.38 g).

Yield: 55%.

30) The amides of Table 1 and 2 are prepared by treating with the same molar ratio of the corresponding starting materials under the amidation condition same with those of above 1) to 29).

EXAMPLE 2

Deacylation

1) To a solution of the corresponding amide in dichloromethane under nitrogen atmosphere and ice cooling are added pyridine (2.2 Eq.) and phosphorus pentachloride (2 Eq.), and the mixture is stirred at room temperature for 1.5 hours. The reaction mixture is cooled at −40° C., added methanol or isobutanol (40 parts), and stirred under ice cooling for 4 hours. The separating crystals are collected by filtration to obtain hydrochloride of the corresponding amino compound.

2) The said hydrochloride is suspended in ethyl acetate, neutralized under ice cooling with aqueous sodium hydrogen carbonate, and extracted with ethyl acetate. The extracted is washed with water, dried, and concentrated under reduced pressure to give amino compound.

3) Amino compounds can be produced by deacylating the corresponding amido compound under the condition as given above.

4) To a solution of 7β-phenylacetamido-3-[4-{3,4-bis(p-methoxybenzyloxy)benzoyl}-1-methylpiperazinio-1-yl]methyl-3-cephem-4-carboxylic acid p-methoxybenzyl ester iodide (6.04 g: 6 mMol.) in dichloromethane (60 ml) are added pyridine (0.72 ml: 1.5 Eq.) and phosphorus pentachloride (1.88 g: 1.3 Eq.) at 0° C., and the mixture is stirred at −10° C. for 1 hour and at 0° C. for 30 minutes. This is cooled at −40° C., diluted with methanol (30 ml) at once and stirred at 0° C. for 1 hour. The reaction mixture is diluted with water and concentrated under reduced pressure. The residue is washed with water and ether and dried to give 7β-amino-3-[4-{3,4-bis(p-methoxybenzyloxy)benzoyl}-1-methylpiperazinio-1-yl]methyl-3-cephem-4-carboxylic acid p-methoxybenzyl ester hydrochloride (2.54 g). Yield: 48%.

IR $\nu$(Nujol) cm$^{-1}$:1784, 1722.

EXAMPLE 3

Salt Formation

1) To a solution of the corresponding carboxylic acid in acetone (10 parts) is added a solution of sodium ethylhexanoate in isobutanol (1 to 2 Eq.), and the mixture is diluted with ethyl acetate and ether. The separating crystals are collected by filtration to give the sodium salt.

2) The corresponding carboxylic acid is suspended in water and adjusted to pH 6.5 with aqueous sodium carbonate. The solution is desalted, poured into vials, and lyophilized in a conventional manner to give sodium salt formulation.

3) The said sodium salt (1 g) prepared by neutralizing under sterile condition is dissolved in distilled water for injection (4 g) and administered to a patient suffering from sensitive pseudomonal bacteria twice a day intravenously to treat this infection.

4) To a suspension of 7β-[2-(2-amino-4-thiazolyl)-2-(1-carboxy-1-methylethoxyimino)acetamido]-3-[4-(3,4-dihydroxybenzoyl)-1-methylpiperazinio-1-yl]methyl-3-cephem-4-carboxylate (7.03 g: 10 mMol.) in water (130 ml) is adjusted to pH 6.4 with N-sodium hydroxide under ice cooling and ultrasonic irradiation. The solution is passed through a membrane filter and lyophilized to give 7β-[2-(2-amino-4-thiazolyl)-2-(1-carboxy-1-methylethoxyimino)acetamido]-3-[4-(3,4-dihydroxybenzoyl)-1-methylpiperazinio-1-yl]methyl-3-cephem-4-carboxylate sodium salt (7.05 g). This is processed to give the vial formulation of Preparation 2.

5) A suspension of 7β-[2-amino-4-thiazolyl)-2-(1-carboxy-1-methylethoxyimino)acetamido]-3-[4-(2-chloro-3,4-dihydroxybenzoyl-1-methylpiperazinio-1-yl]methyl-3-cephem-4-cephem-4-carboxylate (25.0 g: 32.9 mMol.) in water (400 ml) is adjusted to pH 5.5 with aqueous N/2-sodium hydroxide under ice cooling. The solution is passed through a membrane filter and lyophilized to give 7β-[2-(2-amino-4-thiazolyl)-2-(1-carboxy-1-methylethoxyimino)acetamido]-3-[4-(2-chloro-3,4- dihydroxybenzoyl)-1-methylpiperazinio-1-yl]methyl-3-cephem-4-carboxylate sodium salt.

Elemental analysis: Found: C, 43.69; H, 4.40; N, 12.62; Cl, 4.73: S, 8.12; Na, 2.74; $H_2O$, 4.67. Calcd. for $C_{29}H_{31}N_7O_{10}S_2ClNa\ 2\ H_2O$. C, 43.75; H, 4.43; N, 12.31; Cl, 4.45: S, 8.05; Na, 2.89; $H_2O$, 4.52

6) The betaine of Table 1 and the same molar ratio of base as those of above 1) to 5) are treated under the same condition to give the corresponding salts.

EXAMPLE 4

Esterification

1) Diphenylmethyl ester: To a mixed solution of the corresponding carboxylic acid in dichloromethane (10 parts) and methanol (10 parts) is added diphenyldiazomethane (1.2 Eq.). The mixture is stirred at room temperature for 1 hour. The reaction mixture is washed with hydrochloric acid and water, dried, and concentrated under reduced pressure. The residue is recrystallized from ethyl acetate to give diphenylmethyl ester.

2) The ester of Table 2 are prepared by treating the corresponding starting materials of molar ratio and esterification condition the same as that of above 1).

EXAMPLE 5

Deesterification 1) (aluminum chloride) To the corresponding diphenylmethyl ester, t-butyl ester, or p-methoxybenzyl ester are added anisole (12 parts) and aluminum chloride (9 Eq.), and the mixture is stirred at $-40°$ to $0°$ C. for 4 hours. The reaction mixture is mixed with aqueous 5% sodium hydrogen carbonate, filtered to remove solid, and diluted with ethyl acetate. The aqueous layer is separated, acidified with hydrochloric acid, washed with ethyl acetate, and poured onto a column of synthetic adsorbent. The objective product is eluted from the column with 80% methanol to give the carboxylic acid.

2) (trifluoroacetic acid) A solution of the corresponding diphenylmethyl ester, t-butyl ester, or p-methoxybenzyl ester in a mixture of dichloromethane (0.3 to 3 parts), trifluoroacetic acid (0.3 to 3 parts), and anisole (0.5 to 5 parts) is stirred at $-10°$ to $40°$ C. for 10 minutes to 3 hours. The reaction mixture is concentrated under reduced pressure to remove the solvent and reagents. The residue is washed with benzene to give carboxylic acid. When the starting material has t-butoxycarbonylamino, this is deprotected to give trifluoroacetic acid salt of the corresponding amino.

3) (tin tetrachloride) To a solution of the corresponding diphenylmethyl ester, t-butyl ester, or p-methoxybenzyl ester in anisole (10 volumes) is added stannic tetrachloride (15 Eq.), and the mixture is stirred at 0° C. for 24 hours. The reaction mixture is diluted with ice cold ethyl acetate and diluted hydrochloric acid. The aqueous layer is taken and passed through a column of polymer adsorbent HP-20 (16.5 ml) to remove salt. The product is eluted with aqueous methanol. The eluate is lyophilized to give carboxylic acid.

4) (titanium tetrachloride) To a solution of the corresponding diphenylmethyl ester, t-butyl ester, or p-methoxybenzyl ester in dichloromethane (5 to 9 parts) and anisole (2 to 8 parts) keeping at $-10°$ to $10°$ C. is added titanium tetrachloride (3 to 12 Eq.), and the mixture is stirred for 1 to 24 hours). The reaction mixture is treated with aqueous 5% sodium hydrogen carbonate, filtered to remove solid, and diluted with ethyl acetate. The aqueous layer is taken, acidified with hydrochloric acid, washed with ethyl acetate, and passed through a synthetic adsorbent column. The objective product is eluted with 80% methanol to give carboxylic acid. When the starting material has t-butoxycarbonylamino, N-t-butoxycarbonyl-N-methoxyethoxymethylamino, benzyloxycarbonylamino, or the like protected amino, this may be deprotected.

5) (formic acid) To a solution of the corresponding diphenylmethyl ester in anisole (2 to 3 parts) is added 90% formic acid (5 to 6 parts), and the mixture is heated at 50° to 60° C. for 1 to 4 hours to give the carboxylic acid.

6) (p-nitrobenzyl ester: catalytic reduction) To a solution of the corresponding p-nitrobenzyl ester in methanol (10 to 35 parts) and tetrahydrofuran (20 parts) are added 10% palladium carbon (0.15 to 0.22 parts) and 2N-hydrochloric acid (1 part). The mixture is shaken under hydrogen for 2 to 5 hours. The reaction mixture is filtered to remove solid, washed with ethyl acetate, neutralized with aqueous sodium hydrogen carbonate, passed through a column of styrene-divinylbenzene copolymer adsorbent to be desalted, and lyophilized to give the sodium carboxylate salt.

7) (p-nitrobenzyl ester: acid and zinc) To a solution of the corresponding p-nitrobenzyl ester in dichloromethane (60 parts) are added acetic acid (10 parts) and zinc powder (2 parts), and the mixture is stirred at 0° C. for 2 hours. The reaction mixture is filtered to remove solid, diluted with water, and washed with dichloromethane. The aqueous layer is acidified to pH 2 with hydrochloric acid and purified with a column of styrene-divinylbenzene copolymer to give the carboxylic acid.

8) To a stirring solution of aluminum chloride (24.0 g: 15 Eq.) in anisole (240 ml) at $-40°$ C. is added a solution of 7β-2-(2-t-butoxycarbonylamino-4-thiazolyl)-2-(1-t-butoxycarbonyl-1-methylethoxyimino)-acetamido]-3-[4-{3,4-bis(p-methoxybenzyloxy)benzoyl}-1-methylpiperazinio-1-yl]methyl-3-cephem-4-carboxylicacid p-methoxybenzyl ester iodide (16.18 g: 12 mMol.) in dichloromethane (200 ml), and the mixture is stirred at $-40°$ to $-20°$ C. for 1 hour. The reaction mixture is diluted with coldmethanol (200 ml) and N-hydrochloric acid (200 ml). The aqueous layer is taken, washed with dichloromethane, and concentrated under reduced pressure. The residue is passed through a column of styrene-divinylbenzene copolymer (1 liter). The column is washed with water and the product is eluted with 50% methanol. The eluate is concentrated under reduced pressure. The separating solid is collected by filtration and dried to give 7β-[2-(2-aminothiazol-4-yl)-2-(1-carboxy-1-methylethoxyimino)acetamido]-3-[4-(3,4-dihydroxybenzoyl)-1-methylpiperazinio-1-yl]methyl-3-cephem-4-carboxylate (5.24 g). Yield: 62%.

9) To a solution of aluminum chloride (64 g: 9 Eq.) in anisole (328 ml) cooling at $-40°$ C. with stirring is added a solution of 7β-[2-(2-t-butoxycarbonylamino--4-thiazolyl)-2-(1-t-butoxycarbonyl-1-methylethoxyimino(acetamido]-3-[4-(2-chloro-3,4-diacetoxybenzoyl)-1-methylpiperazinio-1-yl]methyl-3-cephem-4-carboxylicacid p-methoxybenzyl ester iodide (65.5 g: 53.4 mMol.) in dichloromethane (400 ml) and the mixture is stirred at $-40°$ to $-20°$ C. for 30 minutes. The reaction mixture is diluted with cold methanol (500 ml( and N-hydrochloric acid (500 ml). The aqueous layer is taken, washed with dichloromethane, and concentrated under reduced pressure. The residue is passed through a column of styrene-divinylbenzene copolymer (700 ml). The column is washed with water and the product is eluted with 70% methanol. The eluate is concentrated under reduced pressure to 1300 ml containing crude 7β-[2-(2-aminothiazol-4-yl)-2-(1-carboxy-1-methylethoxyimino)acetamido]-3-[4-(2-chloro-3,4-diacetoxybenzoyl)1-methylpiperazinio-1-ylmethyl]-3-cephem-4-carboxylate which is subjected to deprotection of Example 11, 5), vide infra.

10) The corresponding starting materials is reacted under the same deesterification condition with the same ratio as that of the said 1) to 9) to give a carboxylic acid or carboxylate of Table 1.

EXAMPLE 6

3-piperazinio introduction

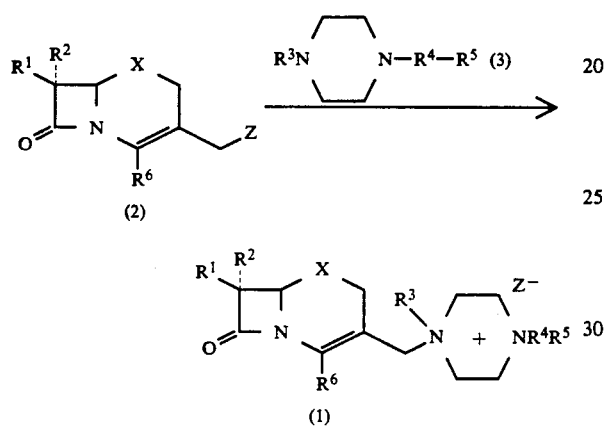

1) To a solution of a leaving group-substituted methyl compound (2) in dichloromethane (2 to 10 parts) is added piperazine (3) (1 to 3 Eq.), and the mixture is let stand at 10° to 50° C. for 1 hour to 1 week. The reaction mixture is washed with water, dried, and concentrated under reduced pressure to give the corresponding piperazinio compound (1).

2) To a solution of a leaving group-substituted methyl compound (2) and sodium iodide (1 to 2 Eq.) in dimethylformamide (2 to 10 parts) is added piperazine (3) (1 to 3 Eq.), and the mixture is stirred overnight at room temperature. The reaction mixture is diluted with dichloromethane, washed with water, dried, and concentrated under reduced pressure to give the corresponding piperazinio compound (1).

3) To a solution of a leaving group-substituted methyl compound (2) and sodium bromide (1 to 2 Eq.) in dimethylformamide (2 to 10 parts) is added piperazine (3) (1 to 3 Eq.), and the mixture is let stand for a week at room temperature. The reaction mixture is diluted with dichloromethane, washed with water, dried, and concentrated under reduced pressure to give the corresponding piperazinio compound (1).

4) To a solution of 7β-[2-(2-t-butoxycarbonylamino-4-thiazolyl)-2-(1-t-butoxycarbonyl-1-methylethoxyimino)acetamido]-3-chloromethyl-3-cephem-4-carboxylic acid p-methoxybenzyl ester 1β-oxide (1) (11.95 g: 15 mMol.) and 4-(3,4-bis(p-methoxybenzyloxy)benzoyl)-1-methylpiperazine (3) (10.0 g: 1.5 Eq.) in dimethylformamide (120 ml) is added sodium iodide (3.37 g: 1.5 Eq.), and the mixture is stirred at room temperature for 3 hours. The reaction mixture is diluted with water. The formed precipitate is collected by filtration, washed with water, dissolved in dichloromethane, washed with water, dried, and concentrated in reduced pressure. The residue is triturated in ether to give 7β-[2--(2-t-butoxycarbonylamino-4-thiazolyl)-2-(1-t-butoxycarbonyl-1-methylethoxyimino)acetamido]-3-[4-{3,4-bis(p-methoxybenzyloxy)benzoyl}-1-methylpiperazinio-1-yl]methyl-3-cephem-4-carboxylic acid p-methoxybenzyl ester iodide 1-β-oxide (1) (19.44 g). Yield: 95%.

5) To a solution of 7β-[2-(2-t-butoxycarbonylamino-4-thiazolyl)-2-(1-t-butoxycarbonyl-1-methylethoxyimino)acetamido]-3-chloromethyl-3-cephem-4-carboxylic acid p-methoxybenzyl ester 1β-oxide (1) (79.6 g: 100 mMol.) and 4-(2-chloro-3,4-diacetoxybenzoyl)-1-methylpiperazine (3) (53.2 g: 1.5 Eq.) in acetone (415 ml) is added sodium iodide (22.5 g: 1.5 Eq.), and the mixture is stirred at room temperature for 2 hours. The reaction mixture is poured into ice cold 0.5N-hydrochloric acid (2.0 liter). The formed precipitate is collected by filtration, washed with water, dissolved in dichloromethane, washed with water, dried, and concentrated in reduced pressure to give 7β-[2-(2-t-butoxycarbonylamino-4-thiazolyl)-2-(1-t-butoxycarbonyl-1-methylethoxyimino)acetamido]-3-[4-(2-chloro-3,4-diacetoxybenzoyl)-1-methylpiperazinio-1-yl]methyl]-3-cephem-4-carboxylic acid p-methoxybenzyl ester iodide 1β-oxide (1) (120 g). Yield 97%.

6) The corresponding starting materials of molar ratio the same as that of the said 1) to 5) is reacted under the same ammonio introduction condition to give a piperazinio compound of Table 1 or 2.

EXAMPLE 7

Introduction of R⁴R⁵

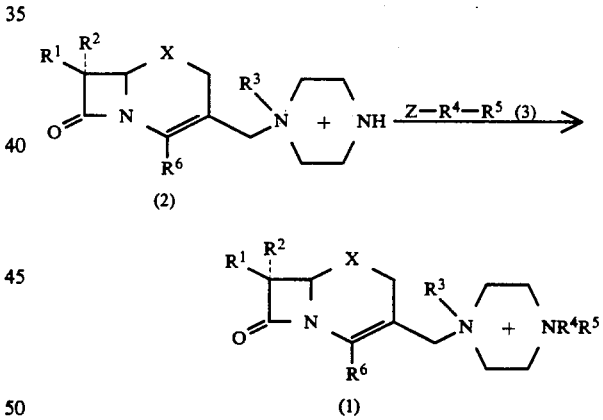

1) (chloride) To a solution of the corresponding 3-piperaziniomethyl compound (2) in dichloromethane (10 parts) is added a solution of 3,4-bis(p-methoxybenzyloxy)benzoyl chloride (3) (1.2 Eq.) in dichloromethane (17 parts), and the mixture is stirred under ice cooling for 3 hours. The reaction mixture is washed with aqueous sodium hydrogen carbonate, dried, and concentrated under reduced pressure. The residual solution is diluted with ether and separating crystals are collected by filtration to give compound (1).

2) (chloride) To a stirred solution of N-methylpiperazine (0.80 g: 2 Eq.) in dimethylformamide (20 ml( at 0° C. is added dimethyl-t-butylchlorosilane (1.21 g). To this solution are added 7β-[2-(2-t-butoxycarbonylamino-4-thiazolyl)-2-(1-t-butoxycarbonyl-1-methylethoxyimino)-acetamido]-3-chloromethyl-3-cephem-4-carboxylic acid p-methoxybenzyl ester 1β- oxide (3.19 g: 4 mMol.) and sodium iodide (1.20 g: 2 Eq.). The mixture is stirred at room temperature for 3 hours. To the reaction mixture is added dilute hydrochloric acid to precipitate 7β-[2-(2-t-butoxycarbonylamino-4-thiazolyl)-2-(1-t-butoxycarbonyl-1-methyl-ethoxyimino)acetamido]-3-(1-methylpiperazinio)-methyl-3-cephem-4-carboxylic acid p-methoxybenzyl ester 1β-oxide (2). This is collected by filtration, washed with water, dissolved in dichloromethane (20 ml), and mixed with acid chloride (3) [prepared from 3,4-bis(p-methoxybenzyloxy)benzoic acid (2.12 g: 1.5 Eq.) and oxalyl chloride in dimethylformamide] and pyridine (0.96 ml: 3.0 Eq.). After 1 hour, the reaction mixture is washed with water, dried, and concentrated under reduced pressure. The residue is washed with ether to give 7β-[2-(2-t-butoxycarbonylamino-4-thiazolyl)-2-(1-t-butoxycarbonyl-1-methylethoxyimino)acetamido]-3-[4-{3,4-bis(p-methoxybenzyloxy)-benzoyl}-1-methylpiperazinio-1-yl]methyl-3-cephem-4-carboxylic acid p-methoxybenzyl ester iodide 1β-oxide (1) (2.62 g). Yield: 48%.

3) The corresponding starting materials of molar ratio the same as that of the said 1) or 2) are reacted under the same condition to give a substituted piperazinio compound of Table 1 or 2.

EXAMPLE 8

Sulfoxide formation 1) (m-chloroperbenzoic acid) To a solution of the corresponding sulfide in a mixture of dichloromethane (10 parts) and methanol (6 parts) is added a solution of 80% m-chloroperbenzoic acid (1.2 Eq.) in a mixture of dichloromethane (17 parts) and methanol (4 parts), and the mixture is stirred for 10 minutes under ice cooling. The separating crystals are collected to give the sulfoxide.

2) (m-chloroperbenzoic acid) To a solution of the corresponding sulfide in chloroform (10 to 20 parts) is added m-chloroperbenzoic acid (1 Eq.) under ice cooling, and the mixture is stirred for 20 to 90 minutes. The reaction mixture is washed with aqueous sodium hydrogen carbonate, dried, and concentrated under reduced pressure to give the sulfoxide.

3) (hydrogen peroxide - polyphosphoric acid) To a solution of the corresponding sulfide in chloroform (10 to 20 parts) are added under ice cooling polyphosphoric acid (0.5 to 1 Eq.) and hydrogen peroxide (1 to 2 Eq.), and the mixture is stirred for 20 to 90 minutes. The reaction mixture is washed with aqueous sodium hydrogen carbonate, dried, and concentrated under reduced pressure to give the sulfoxide.

4) (hydrogen peroxide - tungustic acid) To a solution of the corresponding sulfide in aqueous sodium hydrogen carbonate (10 to 20 parts) is added under ice cooling a catalytic amount of tungustic acid and hydrogen peroxide (1.1 Eq.), and the mixture is stirred for 20 to 90 minutes. The reaction mixture is extracted with chloroform, dried, and concentrated under reduced pressure to give the sulfoxide.

5) (m-chloropherbenzoic acid) To a stirred solution of 7β-[2-(2-t-butoxycarbonylamino-4-thiazolyl)-4-thiazolyl)-2-(1-t-butoxycarbonyl-1-methylethoxyimino)acetamido]-3-[4-{3,4-bis(p-methoxybenzyloxy)-benzoyl}-1-methylpiperazinio-1-yl]methyl-3-cephem-4-carboxylic acid p-methoxybenzyl ester iodide (850 mg: 0.63 mMol.) in dichloromethane (9 ml) at −78° C. is added 80% m-chloroperbenzoic acid (136 mg: 1 Eq.), and the mixture is stirred at −78° to 0° C. The reaction mixture is concentrated under reduced pressure and the formed residue is triturated in ether to give 7β-[2-(2-t-butoxycarbonylamino-4-thiazolyl)-2-(1-t-butoxycarbonyl-1-methylethoxyimino) acetamido]-3-[4-{3,4-bis(p-methoxybenzyloxy)}-1-methylpiperazinio-1-yl]methyl-3-cephem-4-carboxylic acid p-methoxybenzyl ester iodide 1β-oxide (820 mg). Yield: 95%.

6) The corresponding starting materials of molar ratio the same as that of the said 1) to 5) are reacted under the same oxidative condition to give the sulfoxide of Table 1 or 2.

Example 9

Reduction of Sulfoxide 1) (phosphorus tribromide) To a solution of the corresponding sulfoxide in dichloromethane (5 to 50 parts) is added phosphorus tribromide (1 to 3 Eq.) at −40° to −10° C., and the mixture is stirred for 30 minutes to 5 hours at the same temperature. The reaction mixture is diluted with dichloromethane, washed with aqueous sodium hydrogen carbonate and water, dried, and concentrated under reduced pressure to give the sulfide.

2) (phosphorus tribromide) To a solution of the corresponding sulfoxide in dichloromethane (50 parts) and dimethylacetamide (10 parts) at −20° to −25° C. is added a solution of phosphorus tribromide (2.5 Eq.) in dichloromethane (30 parts), and the mixture is stirred at the same temperature for 1 hour 25 minutes. The reaction mixture is diluted with dichloromethane, washed with aqueous sodium hydrogen carbonate and water, dried, and concentrated under reduced pressure to give the sulfide.

3) (potassium iodide) To a stirred solution of the corresponding sulfoxide in acetone (11 parts) are added potassium iodide (6 Eq.) and acetyl chloride (7 Eq.) at −25° C., and the mixture is stirred for 35 minutes. The reaction mixture is diluted with ethyl acetate, washed with aqueous sodium hydrogen sulfite, diluted hydrochloric acid, aqueous sodium hydrogen carbonate, and water, dried, and concentrated under reduced pressure. The residue is purified by silica gel chromatography to give the sulfide.

4) (stannous chloride) To an ice cold solution of the corresponding sulfoxide in N,N-dimethylformamide (12 parts) under nitrogen gas are added stannous chloride (2.5 Eq.) and acetyl chloride (13 Eq.), and the mixture is stirred for 21 hours. The reaction mixture is poured onto ice water and extracted with ethyl acetate. The extract is washed with water and aqueous sodium hydrogen carbonate, dried, and concentrated under reduced pressure. The residue is solidified from a mixture of dichloromethane, benzene, and ether to give a crystalline.

5) 7β-[2-(2-t-butoxycarbonylamino-4-thiazolyl)-2-(1-t-butoxycarbonyl-1-methylethoxyimino)acetamido]-3-[4-(3,4-bis(p-methoxybenzyloxy)-benzoyl)-1-methylpiperazinio-1-ylmethyl]-3-cephem-4-carboxylic acid p-methoxybenzyl ester iodide 1β-oxide (24.56 g: 18 mMol.) in acetone (500 ml) at −30° C. are added potassium iodide (29.88 g: 10 Eq.) and acetyl chloride (7.68 g: 6 Eq.), and the mixture is stirred at −30° to −15° C. for 90 minutes. The reaction mixture is poured onto aqueous 3% sodium sulfite (2.5 liter). The formed precipitate is collected by filtration, washed with water, diluted with dichloromethane, washed with water, dried, and concentrated under reduced pressure to give 7β-[2-(2-t-butoxycarbonylamino-4-thiazolyl)-2-(1-t-butoxycarbonyl-1-methylethoxyimino)acetamido]-3-[4-(3,4-bis(p-methoxybenzyloxy)-benzoyl-1-methylpiperazinio-1-yl]methyl-3-cephem-4-carboxylic acid p-methoxybenzyl ester iodide (22.57 g). Yield: 93%.

6) 7β-[2-(2-t-butoxycarbonylamino-4-thiazolyl)-2-(1-t-butoxycarbonyl-1-methylethoxyimino)acetamido]-3-[4-(2-chloro-3,4-diacetoxybenzoyl)-1-methylpiperazinio-1-yl]methyl-3-cephem-4-carboxylic acid p-methoxybenzyl ester iodide 1β-oxide (120 g: 96.5 mMol.) in acetone (720 ml) at 0° C. are added potassium iodide (160 g: 10 Eq.) and acetyl chloride (45.5 g: 6 Eq.), and the mixture is stirred at 0° to 2° C. for 105 minutes. The reaction mixture is poured onto a solution of sodium sulfite (90 g) in water (4 liter). The resulting precipitate is collected by filtration, washed with water, diluted with dichloromethane, washed with water, dried, and concentrated under reduced pressure to give 7β-[2-(2-t-butoxycarbonylamino-4-thiazolyl)-2-(1-t-butoxycarbonyl-1-methylethoxyimino)acetamido]-3-[4-(2-chloro-3,4-diacetoxybenzoyl)-1-methylpiperazinio-1-yl]methyl-3-cephem-4-carboxylic acid p-methoxybenzyl ester iodide (112.4 g). Yield: 95%.

7) The corresponding starting materials of molar ratio the same as that of the said 1) to 6) are reacted under the same reductive condition to give the sulfide of Table 1 to 2.

Example 10

Protection of Hydroxy 1) (O-benzyloxycarbonyl) To a solution of the corresponding hydroxy compound in dichloromethane (5 to 20 parts) is added benzyl chloroformate (3Eq.), and the mixture is stirred at −20° to 10° C. for 1 to 5 hours. The reaction mixture is diluted with dichloromethane, washed with aqueous sodium hydrogen carbonate and water, dried, and concentrated under reduced pressure. The residue is recrystallized to give O-benzyloxycarbonyl compound.

2) (silyl) To a solution of the corresponding hydroxy compound in N,N-dimethylformamide (5 parts) are added t-butyldimethylsilyl chloride (1 to 2 Eq.) and triethylamine (2 to 3 Eq.), and the mixture is stirred at 0° C. for 1 to 2 hours. The reaction mixture is diluted with ethyl acetate, washed with diluted hydrochloric acid, aqueous sodium hydrogen carbonate, and water, dried, and concentrated under reduced pressure. The residue is purified by silica gel chromatography to give O-t-butyldimethylsilyl compound.

3) (p-methoxybenzyl) To a solution of the corresponding hydroxy compound in acetone (10 to 20 parts) are added p-methoxybenzyl bromide (1 to 3 Eq.) and potassium carbonate (1 to 3 Eq.), and the mixture is stirred at −20° to 10° C. for 1 to 5 hours. The reaction mixture is diluted with dichloromethane, washed with aqueous sodium hydrogen carbonate and water, dried, and concentrated under reduced pressure. The residue is purified by silica gel chromatography and recrystallization to give p-methoxybenzyl ether.

4) The corresponding starting materials of molar ratio the same as that of the said 1) to 3) are reacted under the same protective condition to give the hydroxy-protected compound of Table 1 to 2.

Example 11

Deprotection of Protected Hydroxy 1) (aluminum chloride) To a solution of the corresponding p-methoxybenzyl ether in anisole (12 parts) is added aluminum chloride (9 Eq.), and the mixture is stirred at 0° C. for 4 hours. The reaction mixture is washed with water and diluted hydrochloric acid, dried, and concentrated under reduced pressure to give the phenol.

2) (stannic tetrachloride) To a solution of the corresponding p-methoxybenzyl ether in anisole (10 volumes) is added stannic tetrachloride (15 Eq.), and the mixture is stirred at 0° C. for 24 hours. The reaction mixture is washed with water and hydrochloric acid, dried, and concentrated under reduced pressure to give phenol.

3) (titanium chloride) To a solution of the corresponding p-methoxybenzyl ether in a mixture of dichloromethane (5 to 9 parts) and anisole (2 to 8 parts) is added titanium tetrachloride (3 to 12 Eq.) at −10° to 10° C., and the mixture is stirred for 1 to 24 hours. The reaction mixture is washed with water and hydrochloric acid, dried, and concentrated under reduced pressure to give the phenol.

4) (sodium hydrogen carbonate) To a solution of the corresponding phenol acetate in water (8 ml) containing sodium hydroxide (9 Eq.), and the mixture is stirred at room temperature for 1 to 6 hours. The reaction mixture is neutralized with hydrochloric acid and extracted with dichloromethane. The extract solution is washed with water, dried, and concentrated under reduced pressure to give the phenol.

5) To a crude aqueous suspension of 7β-[2-(2-aminothiazol-4-yl)-2-(1-carboxy-1-methylethoxyimino)acetamido]-3-[4-(2-chloro-3,4-diacetoxybenzoyl)-1-methylpiperazinio-1-yl]methyl-3-cephem-4-carboxylate obtainable by the method of Example 5, 9) is added sodium hydrogen carbonate (26.9 g), and the mixture is stirred for 2 hours. The reaction mixture is diluted with methanol (200 ml) and 2N-hydrochloric acid to adjust to pH 1, passed through a column of styrene-divinylbenzene copolymer (2 liters), washed with water, and eluted with 40% aqueous methanol. The eluate is concentrated under reduced pressure and collecting the resulting crystals to give 7β-[2-(2-aminothiazol-4-yl)-2-(1-carboxy-1-methylethoxyimino)acetamido]-3-[4-(2-chloro-3,4-dihydroxybenzoyl)-1-methylpiperazinio-1-yl]methyl-3-cephem-4-carboxylate (20.0 g). Overall yield from Example 5, 9): 51%.

6) The corresponding starting materials of molar ratio the same as that of the said 1) to 5) are reacted under the same deprotective condition to give the hydroxy compound of Table 1 to 2.

Example 12

Deprotection of Protected Amino 1) (aluminum chloride) To a solution of the corresponding carbobenzoxyamine are added anisol (12 parts) and aluminum chloride (9 Eq.), and the mixture is stirred at 0° C. for 4 hours. The reaction mixture is washed with water and aqueous sodium carbonate, dried, and concentrated under reduced pressure to give the amine.

2) (stannic tetrachloride) To a solution of the corresponding t-butoxycarbonylamine in anisole (10 volumes) is added stannic chloride (15 Eq.) and the mixture is stirred at 0° C. for 24 hours. The reaction mixture is washed with water and aqueous sodium carbonate, dried and concentrated under reduced pressure to give the amine.

3) (titanium tetrachloride) To a solution of the corresponding carbobenzoxyamine in a mixture of dichloromethane (5 to 9 parts) and anisole (2 to 8 parts) is added titanium tetrachloride (3 to 12 Eq.) at $-10°$ to $10°$ C., and the mixture is stirred for 1 to 9 hours. The reaction mixture is washed with water and aqueous sodium carbonate, dried, and concentrated under reduced pressure to give the amine.

4) (thiourea) To a solution of the corresponding chloroacetamide in dichloromethane (5 to 9 parts) is added thiourea, and the mixture is stirred at 0° to 30° C. for 1 to 24 hours. The reaction mixture is washed with water and aqueous sodium carbonate, dried, and concentrated under reduced pressure to give the amine.

5) The corresponding starting materials of molar ratio the same as that of the said 1) to 4) are reacted under the same deprotective condition to give the amino compound of Table 1.

Formulation 1

Ampoule

A sodium salt (1 g) of compound (I) wherein $R^1$ is 2-(2-amino-4-thiazolyl)-2-(1-carboxy-1-methylethoxy)iminoacetamido, $R^2$ is hydrogen, $R^3$ is methyl, $R^4R^5$ is 3,4-dihydroxybenzoyl, $R^6$ is $COO^-$, and X is sulfinyl is dissolved in water for injection (3 ml) and filled with nitrogen in a 5 ml light proof ampoule.

This ampoule preparation is given intramuscularly 1 to 4 times a day to a patient suffering from sensitive *Pseudomonas aeruginosa* infection to cure or releave the infection.

Formulation 2

Vial

A sodium salt (1 g) of compound (I) wherein is 2-(2-amino-4-thiazolyl)-2-(1-carboxy-1-methylethoxy)iminoacetamido, $R^2$ is hydrogen, $R^3$ is methyl, $R^4R^5$ is 3,4-dihydroxybenzoyl, $R^6$ is $COO^-$, and X is sulfur is dissolved in distilled water for injection and poured into a vial. This is freezed at $-30°$ C. by conventional method and lyophilized at 0.01 milli bar keeping the inner temperature at $-20°$ C. This vial formulation is dissolved in distilled water for injection prior to use and administered 1 to 4 times per day intravenously to a patient suffering from sensitive Serratia infection to treat the disease.

Formulation 3

Vial

Sodium salt of Compound (I) (1 g) where $R^1$ is 2-(2-amino-4-thiazolyl)-2-(1-carboxy-1-methylethoxyimino)acetamido, $R^2$ is hydrogen, $R^3$ is methyl, $R^4R^5$ is 3,4-dihydroxyphenyl, $R^6$ is $COO^-$, and X is sulfur is dissolved in distilled water for injection (5 ml) and filled in a vial. This is freezed by conventional method using dry ice and lyophilized at 0.03 millibar keeping the inner temperature at $-20°$ C. This vial formulation is dissolved in a nutrient carrier and dripped 1 to 4 times per day to a patient suffering from sensitive *Klebsiella pneumoniae* infection to treat the disease.

EXPERIMENT 1

Superior Antipseudomonal Activity

The minimal inhibitory concentration (MIC) of Compound (I) or its sodium salt where $R^1$ is 2-(2-amino-4-thiazolyl)-2-(1-carboxy-1-methylethoxyimino)acetamido, $R^2$ is hydrogen, $R^3$ is hydrogen, $R^4$ is methylene, $R^5$ is 3,4-dihydroxyphenyl, $R^6$ is $COO^-$, and X is sulfur, in 0.01N-sodium hydrogen carbonate is determined according to the method of Japan Society of Chemotherapy on agar plate by two fold dilution method to give the MIC value of 0.025 µg/ml against *Pseudomonas aeruginosa* ATCC 25619. By altering the groups with the followings, the activity varied as below (AT=2-amino-4-thiazolyl).

| | MIC µg/ml |
|---|---|
| 7β-Side chain $R^1$ | |
| phenylacetyl | >100 |
| difluoromethylthioacetyl | >100 |
| 2-AT-2-methoxyiminoacetamido | 0.05 |
| 2-AT-2-(1-carboxy-1-vinyloxy)iminoacetamido | 0.05 |
| Cathecol $R^4R^5$ | |
| 3-methoxy-4-hydroxybenzoyl | 3.1 |
| 2-chloro-3,4-dihydroxybenzoyl | 0.02 |
| 5-chloro-3,4-dihydroxybenzoyl | 0.02 |
| 6-chloro-3,4-dihydroxybenzoyl | 0.02 |
| 2,5-dichloro-3,4-dihydroxybenzoyl | 0.02 |
| 4-hydroxy-3-pyridone-2-carbonyl | 0.1 |
| 3,4-dihydroxybenzyl | 0.1 |
| 3,4-dihydroxyphenacyl | 0.05 |
| (2-AT-2-methoxyiminoacetamido) | |

EXPERIMENT 2

Activity and Safety Tests

The 50% effective dose of compound (I) where $R^1$ is 2-(2-amino-4-thiazolyl)-2-(1-carboxy-1-methylethoxy)imino-acetamido, $R^2$ is hydrogen, $R^3$ is methyl, $R^4R^5$ is 3,4-dihydroxybenzoyl, $R^6$ combined with $Y^-$ is a negative charge, X is sulfur for preventing mouse from the death caused by *Pseudomonas aeruginose* SR 24 is 1.25 mg/kg. On intravenous injection, the compound did not show death nor renal toxicity at a dose up to 1 g/kg of a mouse or rabbit.

Preparation A: 3-Ammonio groups

Preparation A-1

A solution of protocatecuic acid (3.08 g: 20 mMol.), potassium carbonate (13.82 g: 5 Eq.), p-methoxybenzyl chloride (15.66 g: 5 Eq.) and sodium bromide (10.29 g: 5 Eq.) in dimethylformamide (31 ml) is kept at room temperature for 3 days to give p-methoxybenzyl 3,4-bis(p-methoxybenzyloxy)benzoate (7.00 g). Yield: 68%

A solution of this product in a mixture of ethanol (20 ml), tetrahydrofuran (10 ml), and 1N-sodium hydroxide is kept at 60° C. for 2 hours to give 3,4-bis(p-methoxybenzyloxy)benzoic acid (5.19 g). Yield: 97%. mp. 171°~172° C.

NMR $(CD_3SOCD_3)\delta$ ppm: 3.75(s, 6H), 5.06(s, 2H), 5.11(s, 2H), 6.91~7.55(m, 11H), 12.33 (brs, 1H).

To a solution of 3,4-bis(p-methoxybenzyloxy)benzoic acid (0.789 g: 2 mMol.) in dichloromethane (8) are added oxalyl chloride (0.26 ml: 1.5 Eq.) and dimethylformamide (catalytic amount), and the mixture is stirred at room temperature for 30 minutes. The reaction mixture is concentrated under reduced pressure leaving the acid chloride. The chloride is dissolved in dichloromethane (10 ml), mixed with N-methyl-piperazine (0.28 ml: 1.25 Eq.) and stirred at room temperature for 1 hour. The reaction mixture is diluted with ethyl acetate, washed with aqueous sodium hydroxide and water, dried, and concentrated under reduced pressure. The residue is purified by silica gel chromatography to give 1-(3,4-bis(p-methoxybenzyloxy)benzoyl)-4-methylpiperazine (0.48 g) from the fraction eluting with 5% methanoldichloromethane. Yield: 50%.

NMR (CDCl₃)δ ppm: 2.32(s, 3H), 2,36(br, 4H), 3.58(br, 4H), 3,81(s, 3H), 3,82(s, 3H), 5.09(s, 2H), 6.86~7.37(m, 11H).

Preparation A-2

2-Chloro-3,4-dihydroxybenzoic acid is p-methoxybenzylated with potassium carbonate and p-methoxybenzyl bromide in dimethylformamide to give p-methoxybenzyl 2-chloro-3,4-bis(p-methoxybenzyloxy)benzoate. This is hydrolyzed with sodium hydroxide to give 2-chloro-3,4-bis(p-methoxybenzyloxy)benzoic acid.

A mixture of 2-chloro-3,4-bis(p-methoxybenzyloxy)benzoic acid (0.61 g: 1.42 mMol.) is reacted with 1-hydroxybenzotriazole (231 mg: 1.2 Eq.) and dicyclohexylcarbodiimide (352 mg: 1.2 Eq.) in tetrahydrofuran at room temperature for 1 hour, and then with N-methylpiperazine (0.32 ml: 2 Eq.) for 1 hour to give 1-(2-chloro-3,4-bis(p-methoxybenzyloxy)benzoyl)-4-methylpiperazine (0.72 g). Yield: 99%.

NMR (CDCl₃)δ ppm: 2.30(s, 3H), ca. 2.3 & 2.47(m, 4H), 3.17, ca. 3.8 (4H), 3.79(s, 3H), 3.83(s, 3H), 4.97, 5.03(ABq, J=10 Hz, 2H), 5.06(s, 2H), 6.79~7.38(m, 11H).

Preparation A-3

To a suspension of 2-chloro-3,4-dihydroxybenzoic acid (12.0 g: 63.6 mMol.) in acetic anhydride (36.4 ml) under ice cooling is added concentrated sulfuric acid (1 drop), and the mixture is stirred for 90 minutes. The reaction mixture is diluted with ice water and resulting precipitate is collected by filtration, washed with water, and dried to give 2-chloro-3,4-diacetoxybenzoic acid (16.68 g). Yield: 96%.

NMR (CDCl₃)δ ppm: 2.33(s, 3H), 2.39 (s, 3H), 7.41 (d, J=8.6 Hz, 1H), 7.79(d, J=8.6 Hz, 1H), ca. 13.5(br, 1H).

To a suspension of 2-chloro-3,4-diacetoxybenzoic acid (16.68 g: 61.2 mMol.) in toluene (100 ml) is added dimethylformamide (47 μl: 0.01 Eq.). To the mixture at 80° to 100° C. is added dropwise thionyl chloride (6.69 ml: 1.5 Eq.), and the mixture is stirred at 100° C. for 30 minutes. The reaction mixture is cooled and concentrated under reduced pressure, diluted with dichloromethane (100 ml) and N-methylpiperazine (8.83 ml), washed with aqueous sodium hydrogen carbonate and water, dried and concentrated under reduced pressure to give 1-(2-chloro-3,4-diacetoxybenzoyl)-4-methylpiperazine (21.3 g). Yield: 98%.

Preparation A-4

A solution of 1-(2-chloro-3,4-diacetoxybenzoyl-4-methylpiperazine (11.06 g: 36.2 mMol.) in methanol (55 ml) is heated under reflux for 5 hours. The reaction mixture is cooled to separate 1-(2-chloro-3,4-dihydroxybenzoyl)-4-methylpiperazine (6.77 g). Yield: 80%.

NMR (D₂O)δ ppm: 2.97(s, 3H), 3.05~3.9 (m, 8H), 6.80~6.99(m, 2H).

Preparation A-5

To a suspension of 1-(2-chloro-3,4-dihydroxybenzoyl)-4-methylpiperazine (0.97 g: 3.58 mMol.) in dichloromethane (10 ml) at 0° C. are added pyridine (0.72 ml: 2.5 Eq.) and trimethylsilyl chloride (1.14 ml: 2.5 Eq.), and the mixture is stirred at room temperature for 10 minutes. The reaction mixture is cooled with ice water, diluted with saturated aqueous sodium hydrogen carbonate. The organic layer is taken, washed with saturated saline, dried, and concentrated in vacuum to give 1-(2-chloro-3,4-di(trimethylsilyloxy)-4-methylpiperazine (1.60 g). Yield: 98%.

NMR (CDCl₃)δ ppm: 0.27(s, 9H), 0.29(s, 9H), 2.38(s, 3H), 2.41~2.60 (m, 4H), 3.27~3.38(m, 2H), 3.73~4.03(m, 2H), 6.78(s, 2H).

Preparation A-6

Ethyl 5-chloro-3,4-dihydroxybenzoate is p-methoxybenzylated with p-methoxybenzyl bromide and potassium carbonate in dimethylformamide to give ethyl 5-chloro-3,4-bis(p-methoxybenzyloxy)benzoate. This is hydrolyzed with sodium hydroxide to give 5-chloro-3,4-di(p-methoxybenzyloxy)benzoic acid.

NMR (CD₃SOCD₃)δ ppm: 3.74(s, 3H), 3.78(s, 3H), 5.01(s, 2H), 5.18 (s, 2H), 6.86(d, J=8.8 Hz, 6.99(d, J=8.8Hz, 2H), 7.28(d, J=8.8Hz, 2H), 7.45(d, J=8.8 Hz, 2H), 7.54(d, J=1.8 Hz, 1H), 7.63(d, J=1.8 Hz, 1H)

To a solution of 5-chloro-3,4-bis(p-methoxybenzyloxy)benzoic acid (0.75 g: 1.75 mMol.) and 1-hydroxybenzotriazole (0.26 g: 1.1 Eq.) in tetrahydrofuran (15 ml) is added dicyclohexylcarbodiimide (0.40 g: 1.1 Eq.). After 1 hour stirring, to the mixture is added N-methylpiperazine (0.44 ml: 2.3 Eq.), and the mixture is stirred for 1 hour. The reaction mixture is filtered to remove solid and concentrated under reduced pressure to give 1-(5-chloro-3,4-bis(p-methoxybenzyloxy)benzoyl)-4-methylpiperazine (0.86 g). Yield: 96%.

NMR (CDCl₃)δ ppm: 2.32(s, 3H), 2.37(br, 4H), 3.45(br, 4H), 3.81(s, 3H), 3.83(s, 3H), 5.00(s, 2H), 5.07(s, 2H), 6.82~7.37(m, 10H).

Preparation A-7

A solution of 3,4-dihydroxy-6-chlorobenzoic acid (48 g: 250 mMol.) in a mixture of toluene (180 ml) and ethanol (180 ml) is heated under reflux under Dean Stark apparatus filled with Molecular Sieves for 12 hours. The reaction mixture is cooled and washed with aqueous sodium hydrogen carbonate and water, dried and concentrated under reduced pressure to give 6-chloro-3,4-dihydroxybenzoic acid ethyl ester (52.7 g). Yield: 95%.

NMR (CD₃SOCD₃)δ ppm: 1.30(t, J=7 Hz, 3H), 4.25(q, J=7 Hz, 2H), 6.84(s, 1H), 7.31(s, 1H).

Preparation A-8

To a solution of 3,4-dihydroxy-6-chlorobenzoic acid ethyl ester (52.7 g: 243 mMol.) in dimethylformamide (170 ml) are added potassium carbonate (105 g; 3.1 Eq.) and p-methoxybenzyl bromide (151 g: 3.1 Eq.), and the mixture is stirred at room temperature for 4 hours. The reaction mixture is diluted with ice water and filtered to collect the resulting precipitate, which is washed with methanol and water to give 6-chloro-3,4-bis(p-methoxybenzyloxy)benzoic acid ethyl ester (110 g). Yield: 99%.

NMR (CDCl₃)δ ppm: 1.34(t, J=7.1 Hz, 3H), 3.81(s, 3H), 3.82(s, 3H), 4.85(q, J=7.1 Hz, 2H), 5.06(s, 2H), 5.08(s, 2H), 6.88(d, J=8.7 Hz, 2H), 6.90(d, J=8.7 Hz, 2H), 7.26(s, 1H), 7.33(d, J=8.7 Hz, 4H), 7.49(s, 1H).

Preparation A-9

A solution of 6-chloro-3,4-bis(p-methoxybenzyloxy)benzoic acid ethyl ester (110 g: 240 mMol.) in a mixture of ethanol (800 ml), pg,64 tetrahydrofuran (150 ml), and aqueous 2N -sodium hydroxide (264 ml: 2.2 Eq.) is heated at 70° C. for 2 hours. The reaction mixture is cooled and acidified with hydrochloric acid. The resulting precipitate is collected by filtration and washed with ethanol and water to give 6-chloro-3,4-bis(p-methoxybenzyloxy)benzoic acid (94 g). Yield: 99%.

NMR (CDCl3) δ ppm: 3.81(s, 3H), 3.82(s, 3H), 5.08(s, 2H), 5.11(s, 2H, 6.91(d, J=8.6 Hz, 2H), 6.89(d, J=8.6 Hz, 2H), 6.99(s, 1H), 7.34(d, J=8.6 Hz, 4H), 7.65(s, 1H).

Preparation A-10

To a solution of 6-chloro-3,4-bis(p-methoxybenzyloxy)benzoic acid (94 g: 218 mMol.) in tetrahydrofuran (1 liter) are added dicyclohexylcarbodiimide (50 g: 1.1 Eq.) and N-hydroxybenzotriazole (33 g: 1.1 Eq.), and the mixture is stirred at room temperature for 90 minutes. To the reaction mixture is added N-methylpiperazine (48 ml: 2 Eq.) and the resulting precipitate is filtered off. The filtrate is concentrated under reduced pressure, diluted with ethyl acetate, washed with aqueous sodium hydroxide and water, dried and concentrated in vacuum. The residue is treated in dichloromethane and ether to remove a small amount of insoluble material and concentrated under reduced pressure to give 1-(6-chloro-3,4-bis(p-methoxybenzyloxy)benzoyl-4-methylpiperazine (108 g). Yield: 97%.

Cl Preparation A-11

To a stirred solution of 3,4-dihydroxybenzoic acid (10 g: 64.88 mMol.) in acetic acid (40 ml) at 50° C. is added sulfuryl chloride (21.2 g; 2.4 Eq.) over 15 minutes, and the mixture is stirred for 17 hours at the same temperature. The reaction mixture is cooled with ice and filtered to collect crystals. The crystals are washed with n-hexane and recrystallized from ethyl acetate-n-hexane to give 2.5-dichloro-3,4-dihydroxybenzoic acid (4.8 g). Yield: 33%. mp. 230°~231° C.

NMR (CD3SOCD3) δ ppm: 7.38(s, 1H).

To a solution of 2,5-dichloro-3,4-dihydroxybenzoic acid (2.4 g) in dimethylformamide (20 ml) are added potassium carbonate (4.90 g: 3.6 Eq.) and p-methoxybenzyl bromide (7.14 g: 3.6 Eq.). To the stirring mixture are added at room temperature every 2 hours potassium carbonate (1.6 g: 1.2 Eq.) and p-methoxybenzyl bromide (2.3 g: 1.2 Eq.). The reaction mixture is poured into ice water and extracted with ethyl acetate. The extract is washed with water, dried, and concentrated under reduced pressure. The residue is purified by silica gel chromatography giving 2.5-dichloro-3,4-bis(p-methoxybenzyloxy)benzoic acid p-methoxybenzyl ester (4.9 g) from the fraction eluting with toluene: ethyl acetate (40:1). Yield: 78%.

To a solution of this product in ethanol (60 ml) and 10% sodium hydroxide is stirred at 50° C. for 2 hours. The reaction mixture is concentrated to remove ethanol, acidified with hydrochloric acid, and extracted with ethyl acetate. The extract is dried and concentrated under reduced pressure. The residue is solidified from n-hexane to give 2,5-dichloro-3,4-bis(p-methoxybenzyloxy)benzoic acid (2.02 g). Yield: 52%.

NMR (CD3SOCD3) δ ppm: 3.82(s, 6H), 5.16(s, 4H), 6.91(d, J=8.5 Hz, 2H), 7.38(d, J=8.5 Hz, 2H), 7.70(s, 1H).

To a solution of 2,5-dichloro-3,4-bis(p-methoxybenzyloxy)benzoic acid (2.02 g: 4.36 mMol.) and 1-hydroxybenzotriazole (648 mg: 1.1 Eq.) in tetrahydrofuran (40 ml) is added dicyclohexylcarbodiimide (990 mg: 1.1 Eq.), and the mixture is stirred at room temperature for 90 minutes. This solution is mixed with N-methylpiperazine (0.66 g: 1.5 Eq.) and stirred at room temperature for 1 hour. The reaction mixture is filtered to remove solid and concentrated under reduced pressure. The residue is purified by silica gel chromatography to give 1-(2,5-dichloro-3,4-bis(p-methoxybenzyloxy)benzoyl)-4-methylpiperazine (1.7 g) from the fraction eluting with 5% methanol-chloroform. Yield: 71%.

NMR (CDCl3) δ ppm: 2.33(s, 3H), 2.33~2.36(m, 4H), 3.83(s, 6H), 3.72~3.93(m, 4H), 4.96~5.14(q, 4H), 6.89(s, 1H), 6.92(d, J=8.8 Hz, 2H), 7.38(d, J=8.8 Hz, 2H).

Preparation A-12

Vanilinic acid ethyl ester is etherified in dimethylformamide with potassium carbonate and p-methoxybenzyl bromide to give ethyl 3-methoxy-4-p-methoxybenzyloxybenzoate. This is hydrolyzed with sodium hydroxide to give 3-methoxy-4-p-methoxybenzyloxybenzoic acid.

A mixture of 3-methoxy-4-p-methoxybenzyloxybenzoic acid (2.88 g: 10 mMol.), 1-hydroxybenzotriazole (1.49 g: 1.1 Eq.), and dicyclohexylcarbodiimide (2.27 g: 1.1 Eq.) in tetrahydrofuran (100 ml) is kept at room temperature for 3 hours. To this solution is added N-methylpiperazine (2.22 ml: 2 Eq.), and the mixture is kept at room temperature overnight to give 1-(3-methoxy-4-p-methoxybenzyloxybenzoyl)-4-methylpiperazine (3.45 g). Yield: 93%.

NMR (CDCl3) δ ppm: 2.33(s, 3H), 2.42(brs, 4H), 3.64(brs, 4H), 3.81 (s, 3H), 3.89(s, 3H), 5.10(s, 2H), 6.88~7.00(m, 5H), 7.36(d, J=8.4 Hz, 2H).

Preparation A-13

To a suspension of kojic acid (50 g: 0.32 Mol.) in dimethylformamide (300 ml) are added potassium carbonate (63 g: 1.42 Eq.) and p-methoxybenzyl bromide (92 g: 1.42 Eq.), and the mixture is stirred at room temperature for 2 hours. The reaction mixture is diluted with water (1liter) to give 5-p-methoxybenzyloxy-2-hydroxymethyl-4-pyrone (74.5 g). Yield: 81%. mp. 124°~130° C.

NMR (CD3SOCD) δ ppm: 3.79(s, 3H), 4.40(s, 2H), 4.94(s, 2H), 6.50(s, 1H), 6.91(d, J=8.8 Hz, 2H), 7.35(d, J=8.8 Hz, 2H), 7.99(s, 1H).

To an ice cold solution of 5-p-methoxybenzyloxy-2-hydroxymethyl-4-pyrone (30 g) in acetone (600 ml) is added dropwise Jones reagent (70 ml), and the mixture is stirred for 2 hours. The resulting crystals are collected by filtration, washed with water and acetone, and dried to given 5-p-methoxybenzyloxy-4-pyrone-2-carboxylic acid (21.86 g). Yield: 69%. d.p.: >230° C.

NMR (CD3SOCD3) δ ppm: 4.91(s, 2H), 6.93(s, 1H), 6.96(d, J=8.6 Hz, 2H), 7.36(d, J=8.6 Hz, 2H), 8.35(s, 1H).

To a solution of 5-p-methoxybenzyloxy-4-pyrone-2-carboxylic acid (1.389 g: 5 mMol) in dichloromethane (20 ml) are added methanesulfonyl chloride (0.41 ml: 1.06 Eq.) and pyridine (0.81 ml: 2 Eq.), and the mixture is stirred at room temperature for 1 hour. To the solution containing methanesulfonic mixed anhydride is added N-methylpiperazine (0.61 ml: 1.1 Eq.), and the mixture is stirred for 2 hours. The reaction mixture is poured into water and extracted with chloroform. The residue is purified by silica gel chromatography to give 1-(5-p-meth-oxybenzyloxy-4-pyrone-2-carbonyl)-4-methylpiperazine (1.363 g) from the fraction eluting with chloroform-methanol (10:1). Yield: 76%. NMR (CDCl$_3$) δ ppm: 2.33(s, 3H), 2.3~2.5(m, 4H), 3.4~3.8(m, 4H), 3.81(s, 3H), 5.03(s, 2H), 6.59(s, 1H), 6.89(d, J=8.5 Hz, 2H), 7.32 (d, J=8.5 Hz, 2H), 7.56(s, 1H).

To a solution of 1-(5-p-methoxybenzyloxy-4-pyrone-2-carbonyl)-4-methylpiperazine (0.944 g) in methanol (4 ml) is added aqueous 28% ammonia (8 ml), and the mixture is kept standing for 2 days. The reaction mixture is concentrated to remove methanol and extracted with chloroform. The extract is concentrated under reduced pressure. The residue is purified by silica gel chromatography to give 1-(5-p-methoxybenzyloxy-4-pyridone-2-carbonyl)-4-methylpiperazine (0.246 g) from the fraction eluting with chloroform-methanol (10:1). Yield: 26%. mp. 190°~195° C.

NMR (CDCl$_3$) δ ppm: 2.31(s, 3H), 2.35~2.55(m, 4H), 3.01(s, 3H), 3.5~3.8(m, 4H), 5.09 (s, 2H), 6.90(d, J=8.4 Hz, 2H), 7.11(s, 1H), 7.33(d, J=8.9 Hz, 2H), 7.94(s, 1H).

Preparation A-14

A solution of N-methylpiperazine (2.77 ml: 1.25 Eq.) and α-chloro-3,4-dihydroxyacetophenone (3.73 g: 20 mMol.) in N,N-dimethylformamide (10 ml) is stirred at room temperature for 3.5 hours in the presence of potassium carbonate (2.76 g: 1 Eq.). The reaction mixture is filtered to remove solid and concentrated under reduced pressure. The residue is solidified by ether to give α-(4-methylpiperazin-1-yl)-3,4-dihydroxyacetophenone (6.07 g).

To an ice cold suspension of 1-(3,4-dihydroxybenzoylmethyl)-4-methylpiperazine (1.25 g: 4.99 mMol.) in dichloromethane (50 ml) are added pyridine (3.62 ml: 9 Eq.) and acetyl chloride (2.84 ml: 9 Eq.), and the mixture is stirred for 1 hour. The reaction mixture is washed with water, dried, and concentrated under reduced pressure. The residue is extracted with ether. The extract is concentrated under reduced pressure to give 1-(3,4-diacetoxybenzoylmethyl)-4-methylpiperazine (739 mg). Yield: 44%.

NMR (CDCl$_3$) δ ppm: 2.317(s, 3H), 2.323(s, 3H), 2.4~2.7(m, 8H), 3.77 (s, 3H), 7.29(d, J=10.2 Hz, 1H), 7.87(d, J=2.1 Hz. 1H), 7.95(dd, J=2 Hz, J=10.2 Hz, 1H).

Preparation A-15

A solution of 3,4-bis(p-methoxybenzyloxy)benzyl chloride (2.58 g: 6.47 mMol.), N-methylpiperazine (777 mg: 1.2 Eq.), and potassium carbonate (893 mg; 1 Eq.) in dimethylformamide (7 ml) is stirred at room temperature for 3 hours. The reaction mixture is filtered to remove solid and concentrated under reduced pressure. The residue is washed with n-hexane to give 1-(3,4-bis(p-methoxybenzyloxy)benzyl)-4-methylpiperazine. Yield: nearly quantitative.

NMR (CDCl$_3$) δ ppm: 2.29(s, 3H), 2.42(brs, 8H), 3.40(s, 2H), 3.81(s, 6H), 5.08(s, 2H), 5.05(s, 2H), 6.74~7.40(m, 11H).

Preparation A-16

A solution of 3,4,5-triydroxybenzoic acid ethyl ester (9.91 g: 50 mMol.), potassium carbonate (34.6 g: 5 Eq.), p-methoxybenzyl chloride (38.9 g: 5 Eq.) in dimethylformamide (100 ml) is stirred at room temperature for 100 hours. The reaction mixture is diluted with water. Resulting precipitate is collected by filtration and washed with water, methanol, and a mixture of ether and n-hexane to give 3,4,5-tris(p-methoxybenzyloxy)benzoic acid ethyl ester as powder (24.5 g). Yield: 98%.

NMR (CDCl$_3$) δ ppm: 1.36(t, J=7.2 Hz, 3H), 3.76(s, 3H, 3.80(s, 6H), 4.33(q. J=7.2 Hz, 2H), 4.99(s, 2H), 5.03(s, 4H), 6.74(d, J=8.6 Hz, 2H), 6.89(d, J=8.8 Hz, 4H), 7.24(d, J=8.6 Hz, 2H, 7.33(d, J=8.8 Hz, 4H), 7.35(s, 2H).

To a suspension of this ethyl ester (24.5 g) in methanol (100 ml) is added aqueous 2N-potassium hydroxide (44 ml: 2 Eq.). The mixture is heated under refluxing for 2 hours. After cooling, the reaction mixture is acidified with hydrochloric acid, and resulting precipitate was collected by filtration, washed with water, and dried to give 3,4, 5-tris(p-methoxybenzyloxy)benzoic acid (21.2 g). Yield: 91%.

NMR (CD$_3$SOCD$_3$) δ ppm: 3.71(s, 3H), 3.75(s. 6H), 4.90(s, 2H), 5.05 (s, 4H), 6.79(d, J=8.2 Hz, 2H), 6.94(d, J=8.2 Hz, 4H), 7.22(d, J=8.2 Hz, 2H), 7.29(s, 2H), 7.36(d, J=8.2 Hz, 4H).

To a solution of 3,4,5-tris(p-methoxybenzyloxy)benzoic acid (2.29 g: 4.32 mMol.) and 1-hydroxybenzotriazole (0.70 g: 1.2 Eq.) in tetrahydrofuran (23 ml) is added N,N'-dicyclohexylcarbodiimide (1.07 g: 1.2 Eq.). The mixture is stirred at room temperature for 2 hours. Then N-methylpiperazine (0.72 ml: 1.5 Eq.) is added to the mixture. After stirring for 1 hour, resulting urea is filtered off and filtrate is concentrated under reduced pressure. The residue is dissolved in ethyl acetate, washed with water, dried, and concentrated. The residue is purified by silica gel chromatography (dichloromethane/methanol) to give N-3,4,5-tris(p-methoxybenzyloxy)benzoyl-N'-methylpiperazine (2.36 g). Yield: 89%.

NMR (CDCl$_3$) δ ppm: 2.31(s, 3H), ca. 2.32(brs. 4H), ca. 3.1~3.8 (brs, 4H), 3.80(s, 3H), 3.82(s, 6H), 4.99(s, 2H), 5.04(s, 4H), 6.64(s, 2H), 6.78(d, J=8.8 Hz, 2H), 6.90(d, J=8.8 Hz, 4H), 7.30(d, J=8.8 Hz, 2H), 7.32(d, J=8.8 Hz, 4H).

Preparation B Nucleus Parts

Preparation B-1

To a solution of 7β-amino-7α-methoxy-3-chloromethyl-1-dethia-1-oxa-3-cephem-4-carboxylic acid diphenylmethyl ester (1 g) in dichloromethane (5 to 10 ml) are added pyridine (2 Eq.) and difluoromethylthioacetyl chloride (1.1 Eq.), and the mixture is stirred for 1.5 hours at −30° C. The reaction mixture is washed with aqueous sodium hydrogen carbonate and water, dried, and concentrated under reduced pressure. The residue is treated with ethyl acetate-ether to give 7β-difluoromethylthioacetamido-7α-methoxy-3-chloromethyl-1-dethia-1-oxa-3-cephem-4-carboxylic acid diphenylmethyl ester (1 g).

NMR (CDCl$_3$) δ ppm: 3.58(s, 5H), 4.50(s, 2H), 4.55(s, 2H), 5.12(s, 1H), 6.92(t, J=54 Hz, 1H), 6.94(s, 1H), 7.25~7.55(m, 11H).

Preparation B-2

To an ice cold solution of 7β-phenylacetamido-3-chloromethyl-3-cephem-4-carboxylic acid p-methoxybenzyl ester (3.0 g; 6.16 mMol.) in dichloro-methane (50 ml) is added m-chloroperbenzoic acid (1.32 g: 1 Eq.), and the mixture is stirred for 1 hour under ice cooling. The reaction mixture is diluted with aqueous 5% sodium thiosulfate and extracted with dichloromethane. The extract is washed with aqueous sodium hydrogen carbonate, dried, and concentrated in vacuum to give 7β-phenylacetamido-3-chloromethyl-3-cephem-4-carboxylic acid p-methoxybenzyl ester 1-oxide (1.66 g). Yield: 53.5%.

NMR (CD₃SOCD₃) δ ppm: 3.53, 3.67(ABq, J=14.3 Hz, 2H), 3.74(s, 3H), 3.68, 3,91(ABq, J=18.4 Hz, 2H), 4.50, 4.66(ABq, J=11.5 Hz, 2H), 4.91(d, J=4.7 Hz, 1H), 5.20, 5.27(ABq, J=12 Hz, 2H), 5.84(dd, J=4.7 Hz, J=8.2 Hz, 1H), 6.93(d, J=8.6 Hz, 2H), 7.37(d, J=8.6 Hz, 2H), 716~7.43(m, 5H), 8.46(d, J=8.2 Hz, 1H).

Preparation B-3

To s suspension of 7β-amino-3-chloromethyl-3-cephem-4-carboxylic acid p-methoxybenzyl ester toluene-p-sulfonate (4.33 g: 8 mMol.) in dichloromethane (40 ml) at 0° C. are added N-methylmorpholine (0.88 g: 1 Eq.), pyridine (0.8 ml: 1.2 Eq.) and 2-(2-t-butoxycarbonylamino-4-thiazolyl)-2-methoxyiminoacetyl chloride (1.2 Eq.). After 30 minutes at 0° C., the reaction mixture is diluted with ethyl acetate, the organic layer is separated, washed with water, dried, and concentrated under reduced pressure. The residue is purified by silica gel chromatography to give 7β-(2-(2-t-butoxycarbonylamino-4-thiazolyl)-2-methoxyimino)acetamido-3-chloromethyl-3-cephem-4-carboxylic acid p-methoxybenzyl ester (4.89 g) from the fraction eluted with toluene-ethyl acetate. Yield: 94%.

NMR δ(CDCl₃) ppm: 1.54(s, 9H), 3.51, 3.68(ABq, J=18 Hz, 2H), 3.82(s, 3H), 4.08(s, 3H), 4.43, 4.58(ABq, J=12 Hz, 2H), 4.51(d, J=5Hz, 1H), 5.20, 5.26(ABq, J=12 Hz, 2H), 6.02(q, J=5 Hz, J=9 Hz, 1H), 6.91(d, J=9 Hz, 2H), 7.21(s, 1H), 7.35(d, J=9 Hz, 2H), 7.41(d, J=9 Hz, 1H), 8.50(brs, 1H).

IR ν(CHCl₃) cm⁻¹: 3490, 1780, 1716, 1680.

Preparation B-4

To a solution of 7β-[2-(2-t-butoxycarbonylamino-4-thiazolyl)-2-methoxyiminoacetamido]-3-chloromethyl-3-cephem-4-carboxylic acid p-methoxybenzyl ester (6.52 g: 10 mMol.) in dichloromethane (65 ml) at −70° C. is added 80% m-chloroperbenzoic acid (2.37 g; 1.1 Eq.), and the mixture is stirred at −70° to 9° C. for 1 hour. The reaction mixture is diluted with ethyl acetate, washed with aqueous sodium hydrogen sulfite, aqueous sodium hydrogen carbonate, and water, dried, and concentrated under reduced pressure. The residue is diluted with ether to give 7β-[2-(2-t-butoxycarbonylamino-4-thiazolyl)-2-methoxyiminoacetamido]-3-chloromethyl-3-cephem-4-carboxylic acid p-methoxybenzyl ester 1β-oxide (6.25 g). Yield: 94%.

NMR δ(CDCl₃) ppm: 1.52(s, 9H, 3.40, 378(ABq, J=18.6 Hz, 2H), 3.79 (s, 3H), 3.97(s, 3H), 4.31, 4.89(ABq, J=13.6 Hz, 2H), 4.62(d, J=4.8 Hz, 1H), 5.18, 5.30(ABq, J=11.6 Hz, 2H), 6.13(dd, J=4.8 Hz, J=9.6 Hz, 1H), 6.89(d, J=8.6 Hz, 2H), 7.22(s, 1H, 7.33(d, J=8.6 Hz, 2H), 7.99(d, J=9.6 Hz, 1H), 9.21(s, 1H).

Preparation B-5

To a solution of 7β-[2-(2-t-butoxycarbonylamino-4-thiazolyl)-2-methoxyiminoacetamido]-3-chloromethyl-3-cephem-4-carboxylic acid p-methoxybenzyl ester (652 mg: 1 mMol.) in acetone (7 ml) is added sodium iodide (450 mg: 3 Eq.), and the mixture is stirred at room temperature for 1 hour. The reaction mixture is diluted with ethyl acetate, washed with water, dried, and concentrated under reduced pressure to give 7β-[2-(2-t-butoxycarbonylamino-4-thiazolyl)-2-methoxyimino) acetamido]-3-iodomethyl-3-cephem-4-carboxylic acid p-methoxybenzyl ester (730 mg). Yield: 98%.

IR ν(CHCl₃) cm⁻¹: 3480, 1784, 1718, 1682.

Preparation B-6

(R⁶=diphenylmethyl)

1) To a suspension of 7β-amino-3-chloromethyl-3-cephem-4-carboxylic acid p-methoxybenzyl ester (1) p-toluenesulfonate (2.705 g: 5 mMol.) in dichloromethane (50 ml) are added at 0° C. N-methylmorpholine (0.55

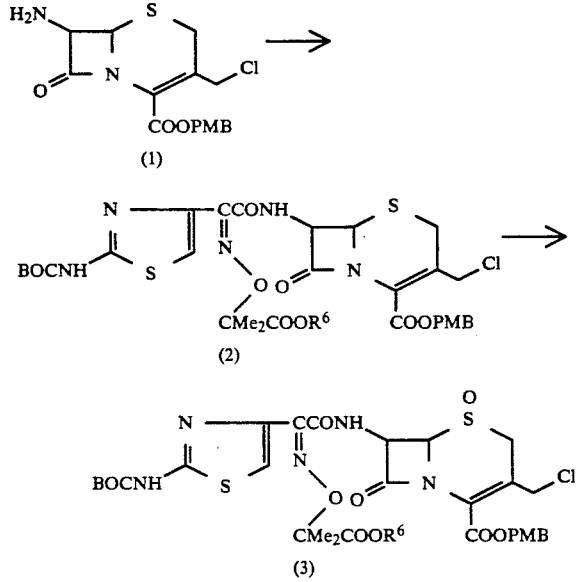

ml: 1 Eq.) and 2-(2-t-butoxycarbonylamino-4-thiazolyl)-2-(1-diphenylmethoxycarbonyl-1-methlethoxyimino)acetic acid (3.51 g: 1.3 Eq.), and the mixture is stirred at −40° C. Then, phenyl dichlorophosphate (0.97 ml: 1.3 Eq.) and N-methylmorpholine (1.65 ml (3 Eq.) are added thereto and stirred at −40° to −10° C. for 1.5 hours. The reaction mixture is diluted with ethyl acetate, washed with water, dilute hydrochloric acid, and water, dried, and concentrated under reduced pressure. The residue is purified by silica gel chromato-graphy to give 7β-[2-(2-t-butoxycarbonylamino-4-thiazolyl)-2-(1-diphenylemthoxycarbonyl-1-methylethoxyimino)acetamido]-3-chloromethyl-3-cephem-4-carboxylic acid p-methoxybenzyl ester (3.70 g) from the fraction eluting with toluene:ethyl acetate. Yield: 83%.

NMR δ(CDCl₃) ppm: 1.55(s, 9H), 1.69(s, 6H), 3.32, 3.56(ABq, J=18 Hz, 2H), 3.87(s, 3H), 4.43, 4.55(ABq, J=12 Hz, 2H), 4.98(d, J=5 Hz, 1H), 5.25(d, J=5 Hz, 2H), 5.99(dd, J=5 Hz, J=9 Hz, 1H), 6.84~7.45(m, 16H).

IR ν(CHCl₃) cm⁻¹: 3490, 1783, 1715, 1680.

2) To a suspension of 7β-amino-3-chloromethyl-3-cephem-4-carboxylic acid p-methoxybenzyl ester hydrochloride (72.1 g: 171 mMol.) in dichloromethane (1200 ml) at 0° C. are added N-methylmorpholine (18.8 ml: 1 Eq.) and 2-(2-t-butoxycarbonylamino-4-thiazolyl)2-(1-diphenylmethoxycarbonyl-1-methylethoxyimino)acetic acid (95.5 g: 1.3 Eq.). To this solution cooled at −40° C. are added phenyl dichloro phosphate (33.2 ml: 1.3 Eq.) and N-methylmorpholine (56.4 ml: 3 Eq.), and the mixture is stirred at −40° to −25° C. for 50 minutes. The reaction mixture is diluted with ice water and the dichloromethane layer is taken. This is washed with hydrochloric acid, water, aqueous sodium hydrogen carbonate, and water, dried, and concentrated under reduced pressure to give 7β-[2-(2-t-butoxycarbonylaminothiazolyl-4-yl)-2-(1-diphenylmethoxycarbonyl-1-methylethoxyimino)acetamido]-3-chloromethyl-3-cephem-4-carboxylic acid p-methoxybenzyl ester (165 g). Yield: 94%

3) To a solution of 7β-[2-(2-t-butoxycarbonylamino-4-thiazolyl)-2-(1-diphenylmethoxycarbonyl-1-methylethoxy)iminoacetamido]-3-chloromethyl-3-cephem-4-carboxylic acid p-methoxybenzyl ester (6.43 g: 7.22 mMol.) in dichloromethane (64 ml) at −78° C. is added m-chloroperbenzoic acid (1.71 g: 1.1 Eq.), and the mixture is gradually warmed to 0° C. The reaction mixture is diluted with ethyl acetate, washed with aqueous sodium sulfite, aqueous sodium hydrogen carbonate, and water, dried, and concentrated under reduced pressure. The residue is purified by silica gel chromatography to give 7β-[2-(2-t-butoxycarbonylamino-4-thiazolyl)-2-(1-diphenylmethoxycarbonyl-1-methylethoxyimino)-acetamido]-3-chloromethyl-3-cephem-4-carboxylic acid p-methoxybenzyl ester 1β-oxide (6.07 g) from the fractions eluting with toluene: ethyl acetate. Yield: 93%.

NMR δ(CDCl$_3$) ppm: 1.53(s, 9H), 1.65(s, 3H), 1.67(s, 3H), 3.34, 3.74 (ABq, J=18.2 Hz, 2H), 3.82(s, 3H), 4.23, 5.01(ABq. J=14.4 Hz, 2H), 4.48 (d, J=4.8 Hz, 1H, 5.27(s, 2H), 6.20 (dd, J=4.8 Hz, J=10 Hz, 1H), ca. 6.9∼7.4(m, 16H), 7.82(d, J=10 Hz, 1H), 8.30(brs, 1H).

IR ν(CHCl$_3$) cm$^{-1}$: 3400, 1802, 1723, 1685.

B. R$^6$=t-butyl.

1) To a solution of 2(2-amino-4-thiazolyl)-2-(1-t-butoxycarbonyl-1-methylethoxyimino)acetic acid (142 g: 43 1 mMol.) and triethylamine (89.7 ml: 1.5 Eq.) in dichloromethane (1.1 l) are added di-t-butyl pyrocarbonate (122 g: 1.3 Eq.) and 4-DMAP (1.05 g: 0.2 Eq.), and the mixture is kept at room temperature for 23 hours. The reaction mixture is concentrated under reduced pressure and diluted with ether. The organic layer is washed with water and extracted with aqueous 5% sodium hydrogen carbonate. The extract is washed with ether, made to pH 2 with hydrochloric acid, and extracted with dichloromethane. The extract is washed with water, dried, and concentrated under reduced pressure. The residue is solidified in isopropanol to give 2-(2-t-butoxycarbonylamino-4-thiazolyl)-2-(1-t-butoxycarbonyl-1-methylethoxyimino)acetic acid (77.93 g). Yield: 42%.

NMR ν(CDCl$_3$) 1.43(s, 9H), 153(s, 9H), 1.58(s, 6H), 7.37(s, 1H).

2) 7β-Amino-3-chloromethyl-3-cephem-4-carboxylic acid p-methoxy-benzyl ester p-toluenesulfonate in dichloromethane is treated with triethylamine, 2-(2-t-butoxycarbonylamino-4-thiazolyl)-2-(1-t-butoxycarbonyl-1-methylethoxyimino)acetic acid, N-methylmorpholine, and phenyl dichloro phosphate to give p-methoxybenzyl 7β-[2-(2-t-butoxycarbonylamino-4-thiazolyl)-2-(1-t-butoxycarbonyl-1-methylethoxyimino)acetamido]-3-chloromethyl-3-cephem-4-carboxylate.

NMR ν(CDCl$_3$) ppm: 1.53(s, 9H), 1.61(s, 3H), 1.64(s, 3H), 3.49, 3.64 (ABq, J=17.6 Hz, 2H), 3.82(s, 3H), 4.46, 4.54(ABq, J=11.8 Hz, 2H), 5.05 (d, J=5 Hz, 1H), 5.21, 5.27(ABq, J=11.2 Hz, 2H), 6.20(dd, J=5 Hz, J=10 Hz, 1H), 6.91(d, J=8 Hz, 2H), 7.19(s, 1H), 7.35(d, J=8 Hz, 2H), 8.20(d, J=10 Hz, 2H).

3) 7β-[2-(2-t-Butoxycarbonylamino-4-thiazolyl)-2-(1-t-butoxycarbonyl-1-methylethoxyimino)acetamido]-3-chloromethyl-3-cephem-4-carboxylic acid p-methoxybenzyl ester in dichloromethane at −78° C. to 0° C. is oxidized with m-chloroperbenzoic acid to give 7β-[2-(2-t-butoxycarbonylamino-4-thiazolyl)-2-(1-t-butoxycarbonyl-1-methylethoxyimino)acetamido]-3-chloromethyl-3-chloromethyl-3-cephem-4-carboxylic acid p-methoxybenzyl ester 1β-oxide.

NMR δ(CDCl$_3$) ppm: 1.42(s, 9H), 1.53(s, 9H), 1.58(s, 3H), 1.60(s, 3H), 3.42, 3.82 (ABq. J=18.9 Hz. 2H), 3.82(s, 3H), 4.23, 5.05 (ABq, J=12.6 Hz, 2H), 4.58(d, J=5 Hz, 1H), 5.25, 5.29(ABq, J=11 Hz, 2H), 6.21(dd. J=5 Hz, J=10 Hz, 1H), 6.92(d, J=8 Hz, 2H), 7.29(s, 1H), 7.36(d, J=8 Hz, 2H), 7.90(d, J=10 Hz, 1H).

Preparation B-7

1) To a solution of 7β-amino-3-chloromethyl-3-cephem-4-carboxylic acid p-methoxybenzyl ester hydrochloride (5.06 g: 12 mMol.) in dichloromethane (100 ml) is added 2-(2-t-butoxycarbonylaminothiazolyl-4 -yl)-2-(t-butoxycarbonyl)vinyloxyimino)acetic acid (5.11 g: 1.03 Eq.). The mixture is cooled to −35° C., mixed with 4-methymorpholine (7.9 ml: 6 Eq.) and monophenyl phosphate dichloride (2.24 ml: 1.31 Eq.), and stirred at −20° to −35° C. for 80 minutes. The reaction mixture is diluted with aqueous 10% citric acid and extracted with ethyl acetate. The extract is washed with aqueous 5% sodium hydrogen carbonate and saturated saline, dried, and concentrated under reduced pressure. The residue is purified by silica gel chromatography to give 7β-[2-(2-t-butoxycarbonylaminothiazolyl-4-yl)-2-(1-(t-butoxycarbonyl)vinyloxyimino) acetamido]-3-chloromethyl-3-chloromethyl-3-cephem-4-carboxylic acid p-methoxybenzyl ester (5.67 g) from the fraction eluting with toluene-ethyl acetate (3:1). Yield: 57%.

NMR (CDCl$_3$) δ ppm: 1.48(s, 9H), 1.48, 3.63(ABq, J=18.5 Hz, 2H), 3.82(s, 3H), 4.46, 4.51(ABq J=13 Hz, 2H), 5.06(d, J=5 Hz, 1H), 5.21, 5.25(ABq, J=11.5 Hz, 2H), 5.60(d, J=1.6 Hz, 1H), 5.76(d, J=1.6 Hz, 1H), 5.94(dd, J=5 Hz, J=8.6 Hz, 1H), 6.90(d, J=8.8 Hz, 2H), 7.36 (d, J=8.8 Hz, 2H), 7.46(s, 1H), 7.99(d, J=8.6 Hz, 1H), 8.44(brs, 1H).

2) To a solution of 7β-(2-(2-t-butoxycarbonylaminothiazolyl-4-yl)-2-(1-(t-butoxycarbonyl)vinyloxyimino)acetamido)-3-chloromethyl-3-cephem-4-carboxylic acid p-methoxybenzyl ester (3.38 g: 4.42 mMol.) in dichloromethane (35 ml) is added m-chloroperbenzoic acid (purity 80%: 955 mg: 1 Eq.) under cooling, and the mixture is stirred at −40° C. for 40 minutes. The reaction mixture is diluted with 5% sodium thiosulfate and extracted with ethyl acetate. The extract is washed with water and saturated saline and concentrated under reduced pressure to give 7β-[2-(2-t-butoxycarbonylaminothiazolyl-4-yl)-2-(1-(t-butoxycarbonyl)-1-vinyloxyimino)acetamido]-3-chloromethyl-3-cephem-4-carboxylic acid p-methoxybenzyl ester 1-oxide (3.23 g). Yield: 94%.

NMR (CDCl$_3$) δ ppm: 1.50(s, 9H), 1.53(s, 9H, 3.40, 3.77(ABq, J=18 Hz, 2H), 3.82(s, 3H), 4.26, 5.00(ABq, J=15 Hz, 2H), 4.65(d, J=5 Hz, 1H), 5.24, 5.30(ABq, J=12 Hz, 2H), 5.47 (d, J=1.8 Hz, 1H), 5.59(d, J=1.8 Hz, 1H), 6.20 (dd, J=5 Hz, J=10 Hz, 1H), 6.92(d, J=8.8 Hz, 2H), 7.36(d, J=8.8 Hz, 2H), 7.39(s, 1H), 7.79 (d, J=10 Hz, 1H), 8.88(brs, 1H).

TABLE 1

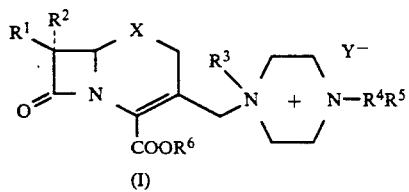

(I)

| No. | R¹ | R⁴ | R⁵ | X | IR: ν (KBr) | NMR: δ ($D_2O$—DCl) ppm |
|---|---|---|---|---|---|---|
| | | | Physical constants of betaines (1) ($R^2$=hydrogen, $R^3$=methyl, $R^6$+$Y^-$=—) | | | |
| 1 | FMX | CO | 3,4-(OH)₂—PH | MO | nd. | 3.22(s, 3H), 3.4~4.5(complexed), 3.60(s, 3H), 3.66(brs, 2H), 4.00, 4.50(ABq, J=14.1Hz, 2H), 5.54(s, 1H), 6.84~7.08(m, 3H), 7.03(t, J=56Hz, 1H). |
| 2 | G | CO | 3,4-(OH)₂—PH | S | 1775, 1660. | 3.14(s, 3H), 3.35~4.30(m, 10H), 3.60(s, 2H), 4.06, 5.05(ABq, J=14Hz, 2H), 5.16(d, J=5Hz, 1H), 5.66(d, J=5Hz, 1H), 6.82~6.97(m, 3H), 7.22~7.88(m, 5H). [$CD_3OD$] |
| 3 | CTX | CO | 3,4-(OH)₂—PH | S | nd. | 3.03(s, 3H), 3.44, 3.70(ABq, J=16.8Hz, 2H), ca. 3.3~4.2(brm, 8H), 3.84(s, 3H), 4.20, 4.66(ABq, J=13.4Hz, 2H), 5.21(d, J=4.8Hz, 1H), 5.57(d, J=4.8Hz, 1H), 6.74(s, 2H), 6.78(s, 1H), 6.93(s, 1H). |
| 4 | CTX | CO | 5-OH-4-pyridone-2- | S | nd. | 3.06(s, 3H), 3.30~4.70(m, 12H), 3.85(s, 3H), 5.19(d, J=4.9Hz) 1H), 5.61(d, J=4.9Hz, 1H), 6.94(s, 1H), 7.25(s, 1H), 8.02(s, 1H). |
| | | | Physical constants of betaines (2) | | | |
| 5 | CTX | CO | 5-OH-4-pyridone-2- | SO | 3300, 1785, 1620, 1530, 1455, 1380. | 3.30(s, 3H), 3.5~4.3(m, 8H), 3.90, 4.20(ABq, J=15.8Hz, 2H), 4.11(s, 3H), 4.94(s, 2H), 5.12(d, J=13Hz, 1H), 5.23(d, J=4.9Hz, 1H), 6.14(d, J=4.9Hz, 1H), 7.20(s, 1H), 7.49(s, 1H), 8.26(s, 1H). |
| 6 | CTX | COCH₂ | 3,4-(OH)₂—PH | S | nd. | 3.43(s, 3H), 3.71, 3.95(ABq, J=17.2Hz, 2H), ca. 4.05(brs, 8H), 4.09(s, 3H), 4.58, 4.65(2 signals of ABq at higher magnetic field, J=14Hz, 1H), 5.11(s, 2H), 5.45(d, J=5Hz, 1H), 5.85(d, J=5Hz, 1H), 7.02(d, J=8.2Hz, 1H), 7.17(s, 1H), 7.48(d, J=2Hz, 1H), 7.51(dd, J=2Hz, J=8.2Hz, 1H). |
| 7 | CTX | CH₂ | 3,4-(OH)₂—PH | S | 1765, 1660. | 3.60~4.04(m, 2H), 4.08(s, 3H), 4.45(s, 2H), 4.85, 5.05(ABq, J=18Hz, 2H), 5.44(d, J=5Hz, 1H), 5.80(d, J=5Hz, 1H), 6.99(s, 2H), 7.07(s, 1H), 7.18(s, 1H). |
| 8 | CAZ | CO | 3,4-(OH)₂—PH | S | 1777, 1670sh, 1615 | 1.63(s, 6H), 3.23(s, 3H), 3.65, 3.95(ABq, J=17.4Hz, 2H), 3.5~4.5(complex), 6.45(d, J=5Hz, 1H), 5.78(d, J=5Hz, 1H), 6.87~6.99(m, 3H), 7.16(s, 1H). |
| | | | Physical constants of betaines (3) | | | |
| 9 | CAZ | CO | 3,4-(OH)₂-2-Cl—PH | S | nd. | 1.62(s, 6H), 3.25(s, 3H), ca. 3.4~4.9(complexed), 5.43(d, J=5Hz, 1H), 5.87(d, J=5Hz, 1H), 6.82~6.99(m, 2H), 7.21(s, 1H). |
| 10 | CAZ | CO | 3,4-(OH)₂-2-Cl—PH | SO | nd. | 1.64(s, 3H), 1.65(s, 3H), 3.25(s, 3H), ca. 3.3~5.1(complex), 5.22(d, J=4.9Hz, 1H), 6.19(d, J=4.9Hz, 1H), 6.87~6.99(m, 2H), 7.24(s, 1H). |
| 11 | CAZ | CO | 3,4-(OH)₂-5-Cl—PH | S | nd. | 1.63(s, 6H), 3.23(s, 3H), ca. 3.5~4.5(m, 8H), 3.65, 3.95(ABq, J=17.2Hz, 2H), 4.34, 4.41(2 signals of ABq at higher magnetic field, J=14Hz, 1H), 5.46(d, J=5.2Hz, 1H), 5.80(d, J=5.2Hz, 1H), 6.94~7.08(m, 3H), 7.18(s, 1H). |
| 12 | CAZ | CO | 3,4-(OH)₂-6-Cl—PH | S | nd. | 1.49(brs, 6H), 3.11(brs, 3H), 3.4~4.6(m, 12H), 5.29(d, J=5Hz, 1H), 5.74(d, J=5Hz, 1H), 6.75~6.99(m, 1H), 6.91(s, 1H), 7.08(s, 1H). |
| 13 | CAZ | CO | 3,4-(OH)₂-2,5-Cl₂—PH | S | 1770, 1660sh | 1.63(s, 6H), 3.29(s, 3H), 3.44~4.04, 4.34~4.65(m, 10H), 4.81~5.04(m, 2H), 5.43~5.50(m, 1H), 5.85(d, J=5Hz, 1H), 7.07(s, 1H), 7.11(s, 1H), 7.22(s, 1H). |
| | | | Physical constants of betaines (4) | | | |
| 14 | CAZ | CO | 4-OH-3-MeO—PH | S | nd. | 1.63(s, 6H), 3.24(s, 3H), ca. 3.5~4.5(m, 8H), 3.63, 3.95(ABq, J=16.6Hz, 2H), 3.89(s, 3H), 4.35, 4.93(ABq, J=13.6Hz, 2H), 5.44(d, J=5.2Hz, 1H), 5.80(d, J=5.2Hz, 1H), 6.97(s, 2H), 7.11(s, 1H), 7.17(s, 1H) |
| 15 | CAZ | CH₂ | 3,4-(OH)₂—PH | S | 1765, 1660. | 1.62(s, 6H), 3.41(s, 3H), 3.75, 3.95(ABq, J=17Hz, 2H), 3.84(brs, 8H), 4.45(s, 2H), 4.61, 4.96(ABq, J=13.5Hz, 2H), 5.47(d, J=5Hz, 1H), 5.86(d, J=5Hz, 1H), 6.99(s, 1H), 7.07(s, 1H), 7.23(s, 1H). |
| 16 | CAZ | CO | 3,4,5-(OH)₃—PH | S | nd. | 1.63(s, 6H), 3.24(s, 3H), 3.5-4.5(brd, 8H), 3.65, 3.95(ABq, J=17.2Hz, 2H), 4.33, 4.40(2 peaks of ABq in higher magnetic field, 1H), 5.45(d, J=5Hz, 1H), 5.82(d, J=5Hz, 1H), 6.60(s, 1H), 7.19(s, 1H). |
| 17 | ENL | CO | 3,4-(OH)₂—PH | S | 3360, 1775, 1660, 1610, 1526, 1385, 1290. | 3.08(brs, 3H), 3.3~4.4(complexed), 5.06, 5.13(2 signals of ABq at higher magnetic field, 1H), 5.16(d, J=5Hz, 1H), 5.28(brs, 1H), 5.44(brs, 1H), 5.72(d, J=5Hz, 1H), 6.79(brs, 2H), 6.89(brs, 1H), 6.98(s, 1H) [$CD_3SOCD_3$—$CD_3OD$]. |

TABLE 2

Physical constants of the protected compounds

| No. | R¹ | R⁴ | R⁵ | R⁶ | X | Y | IR: ν (CHCl₃) cm⁻¹ |
|---|---|---|---|---|---|---|---|
| 1 | FMX | CO | 3,4-(OPMB)₂-PH | BH | MO | I | 3400, 1797, 1700sh, 1685. |
| 2 | G | CO | 3,4-(OPMB)₂-PH | PMB | S | I | 1788, 1725, 1680. |
| 3 | G | CO | 3,4-(OPMB)₂-PH | PMB | SO | I | 1800, 1720, 1680. |
| 4 | BOCCTX | CO | 3,4-(OPMB)₂-PH | PMB | S | I | 3400, 1790, 1723, 1678. |
| 5 | BOCCTX | CO | 3,4-(OPMB)₂-PH | PMB | SO | I | 3400, 1804, 1723, 1680. |
| 6 | BOCCTX | COCH₂ | 3,4-(OAc)₂-PH | PMB | S | I | 3400, 1780, 1723, 1690. |
| 7 | BOCCTX | COCH₂ | 3,4-(OAc)₂-PH | PMB | SO | I | 1805, 1730, 1680. |
| 8 | BOCCTX | CH₂ | 3,4-(OPMB)₂-PH | PMB | S | I | 1778, 1720, 1670. [Nujol] |
| 9 | BOCCTX | CH₂ | 3,4-(OPMB)₂-PH | PMB | SO | I | 1800, 1720, 1680. |
| 10 | BOCCTX | CO | 5-OPMB-4-pyridone-2- | PMB | S | I | nd. |
| 11 | BOCCTX | CO | 5-OPMB-4-pyridone-2- | PMB | SO | I | nd. |
| 12 | BOCCAZBH | CO | 3,4-(OPMB)₂-PH | PMB | S | I | 1792, 1723, 1680. |
| 13 | BOCCAZBH | CO | 3,4-(OPMB)₂-PH | PMB | SO | I | 3400, 1804, 1723, 1685sh. |
| 14 | BOCCAZtBu | CO | 3,4-(OPMB)₂-PH | PMB | S | Cl | 1793, 1724, 1680. |
| 15 | BOCCAZtBu | CO | 3,4-(OPMB)₂-PH | PMB | S | I | 1794, 1723, 1680. |
| 16 | BOCCAZtBu | CO | 3,4-(OPMB)₂-PH | PMB | SO | I | 3400, 1805, 1722, 1685sh. |
| 17 | BOCCAZtBu | CO | 3,4-(OAc)₂-2-Cl-PH | PMB | S | I | 3400, 1782, 1720. |
| 18 | BOCCAZtBu | CO | 3,4-(OAc)₂-2-Cl-PH | PMB | SO | I | 3400, 1803, 1724. |
| 19 | BOCCAZtBu | CO | 3,4-(OPMB)₂-2-Cl-PH | PMB | S | I | 1798, 1725, 1682. |
| 20 | BOCCAZtBu | CO | 3,4-(OPMB)₂-2-Cl-PH | PMB | SO | I | 3400, 1806, 1724. |
| 21 | BOCCAZtBu | CO | 3,4-(OPMB)₂-5-Cl-PH | PMB | S | I | 1796, 1724, 1680. |
| 22 | BOCCAZtBu | CO | 3,4-(OPMB)₂-5-Cl-PH | PMB | SO | I | 3380, 1808, 1727, 1690sh. |
| 23 | BOCCAZtBu | CO | 3,4-(OPMB)₂-6-Cl-PH | PMB | S | I | 3400, 1795, 1724. |
| 24 | BOCCAZtBu | CO | 3,4-(OPMB)₂-6-Cl-PH | PMB | SO | I | 3400, 1725, 1723. |
| 25 | BOCCAZtBu | CO | 3,4-(OPMB)₂,5-5-Cl₂-PH | PMB | S | I | 1783, 1712. |
| 26 | BOCCAZtBu | CO | 3,4-(OPMB)₂,5-5-Cl₂-PH | PMB | SO | I | 1795, 1715. [Nujol] |
| 27 | BOCCAZtBu | CO | 4-OPMB-3-MeO-PH | PMB | S | I | 3400, 1796, 1720, 1683. |
| 28 | BOCCAZtBu | CO | 4-OPMB-3-MeO-PH | PMB | SO | I | 3400, 1806, 1723, 1677. |
| 29 | BOCCAZtBu | CH₂ | 3,4-(OPMB)₂-PH | PMB | S | I | 1785, 1720, 1675. |
| 30 | BOCCAZtBu | CH₂ | 3,4-(OPMB)₂-PH | PMB | SO | I | 1800, 1720, 1685. |
| 31 | BOCCAZtBu | CO | 3,4,5-(OPMB)₃-PH | PMB | S | I | 3400, 1792, 1720, 1680sh. |
| 32 | BOCCAZtBu | CO | 3,4,5-(OPMB)₃-PH | PMB | SO | I | 3480, 1805, 1722, 1690sh. |
| 33 | BOCENLtBu | CO | 3,4-(OPMB)₂-PH | PMB | S | Br | |
| 34 | BOCENLtBu | CO | 3,4-(OPMB)₂-PH | PMB | SO | Br | |

| No. | NMR: δ(CDCl₃) ppm |
|---|---|
| 1 | nd. |
| 2 | nd. |
| 3 | nd. |
| 4 | nd. |
| 5 | nd. |
| 6 | nd. |
| 7 | nd. |
| 8 | nd. |
| 9 | nd. |
| 10 | nd. |
| 11 | nd. |
| 12 | nd. |
| 13 | nd. |
| 14 | nd. |
| 15 | nd. |
| 16 | nd. |
| 17 | nd. |
| 18 | nd. |
| 19 | nd. |
| 20 | nd. |
| 21 | nd. |
| 22 | nd. |
| 23 | nd. |
| 24 | nd. |
| 25 | nd. |
| 26 | nd. |
| 27 | nd. |
| 28 | nd. |
| 29 | nd. |
| 30 | nd. |
| 31 | nd. |
| 32 | nd. |
| 33 | 1.51(s, 9H), 1.54(s, 9H), 3.16(brs, 3H), 3.4~4.3(complexed), 3.78(s, 3H), 3.80(s, 3H), 3.82(s, 3H), 4.66, 4.88(ABq, J=16Hz, 2H), 5.05~5.32(complexed), 5.37(d, J=5Hz, 1H), 5.52 (d, J=1.6Hz, 1H), 5.68(d, J=1.6Hz, 1H), 5.87(d, J=5Hz, 1H), 6.8~7.45(m, 15H). |
| 34 | 1.51(s, 9H), 1.55(s, 9H), 3.18(brs, 3H), 3.1~4.4(complexed), 3.80(s, 3H), 3.82(s, 3H), 3.83(s, 3H), 5.10(s, 2H), 5.12(s, 2H), 5.25, 5.32(ABq, J=11Hz, 2H), 5.28(d, J=5Hz, 1H), 5.51(d, J=1.6Hz, 1H), 5.63(d, J=1.6Hz, 1H), 6.20(d, J=5Hz, |

TABLE 2-continued

Physical constants of the protected compounds

1H), 6.85~7.10(m, 9H), 7.3~7.45(m, 6H).

IR: nd.

TABLE 3

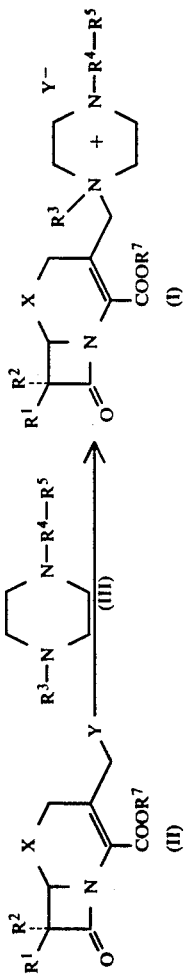

$R^2 = H, R^3 = Me$

[Procedure] To a solution of Compound (II) and Amine (III) in Solvent is added Reagent, and the mixture is stirred at indicated Temp and Time. The reaction mixture is diluted with water and precipitate is collected to give product (I).

| | | Compound (II) | | | | | Amine (III) | | Reagent | Solvent | | Temp | Time | Product Crop Yield | |
|---|---|---|---|---|---|---|---|---|---|---|---|---|---|---|---|
| $R^1$ | $R^4$ | $R^5$ | $R^7$ | X | Y | mg | mg/Eq. | | mg/Eq. | | ml | °C. | min. | mg | % |
| *Introduction of Piperazinio (1)* | | | | | | | | | | | | | | | |
| FMX | CO | 3,4-(OPMB)₂—PH | BH | MO | Cl→I | 1106 | 1430/1.5 | NaI | 450/1.5 | DMF | 11 | rt | 60 | 1680 | 75 |
| G | CO | 3,4-(OPMB)₂—PH | PMB | SO | Cl→I | 1600 | 1970/1.3 | NaI | 525/1.5 | DMF | 50 | rt | 420 | 3150 | 93 |
| BOCCTX | CO | 3,4-(OPMB)₂—PH | PMB | SO | Cl→I | 668 | 700/1.47 | NaI | 150/1 | DMF | 4 | rt | 120 | 1165 | 94 |
| BOCCTX | CO | 5-OPMB-4-pyridone-2- | PMB | S | I→I | 193 | 71/0.8 | — | — | DMF | 0.5 | rt | 25 | 77 | 34 |
| BOCCTX | CO | 5-OPMB-4-pyridone-2- | PMB | SO | I→I | 180 | 71/0.87 | — | — | DCM | 0.5 | rt | 60 | 211 | 93 |
| BOCCTX | COCH₂ | 3,4-(OAc)₂—PH | PMB | SO | Cl→I | 1336 | 1003/1.5 | NaI | 330/1.1 | DMF | 13 | rt | 210 | 2000 | 91 |
| BOCCTX | CH₂ | 3,4-(OPMB)₂—PH | PMB | SO | Cl→I | 1000 | 900/1.3 | NaI | 247/1.1 | DMF | 6 | rt | 240 | 1800 | 98 |
| BOCCAZtBu | CO | 3,4-(OPMB)₂—PH | PMB | SO | Cl→I | 11950 | 10000/1.5 | NaI | 3370/1.5 | DMF | 120 | rt | 180 | 19440 | 95 |
| *Introduction of Piperazinio (2)* | | | | | | | | | | | | | | | |
| BOCCAZtBu | CO | 3,4-(OAc)₂-2-Cl—PH | PMB | SO | Cl→I | 7960 | 5320/1.5 | NaI | 2250/1.5 | An | 42 | rt | 120 | 12000 | 97 |
| BOCCAZtBu | CO | 3,4-(OPMB)₂-2-Cl—PH | PMB | SO | Cl→I | 796 | 689/1.35 | NaI | 202/1.35 | DMF | 4 | rt | 180 | 1350 | 97 |
| BOCCAZtBu | CO | 3,4-(OPMB)₂-5-Cl—PH | PMB | SO | Cl→I | 956 | 940/1.53 | NaBr | excess | An | 5 | rt | 1440 | 1367 | 87 |
| BOCCAZtBu | CO | 3,4-(OPMB)₂-6-Cl—PH | PMB | SO | Cl→I | 9800 | 10600/1.68 | NaI | 3000/1.63 | DMF | 350 | rt | 240 | 16200 | 94 |
| BOCCAZtBu | CO | 3,4-(OPMB)₂-2,5-Cl₂PH | PMB | SO | Cl→I | 1080 | 1000/1.35 | NaI | 270/1.1 | DMF | 10 | rt | 180 | 1540 | 73 |
| BOCCAZtBu | CO | 4-OPMB-3-OMe—PH | PMB | SO | Cl→I | 1593 | 1200/1.62 | NaI | 450/1.5 | DMF | 8 | rt | 120 | 2480 | 99 |
| BOCCAZtBu | CH₂ | 3,4-(OPMB)₂—PH | PMB | SO | Cl→I | 1320 | 1000/1.3 | NaI | 275/1.1 | DMF | 7 | rt | 180 | 2070 | 92 |
| BOCCAZtBu | CO | 3,4,5-(OPMB)₃—PH | PMB | SO | Cl→I | 1990 | 2300/1.5 | NaI | 560/1.5 | DMF | 20 | rt | 120 | 3600 | 93 |
| BOCCAZBH | CO | 3,4-(OPMB)₂—PH | PMB | SO | Cl→I | 725 | 572/1.5 | NaI | 150/1.25 | DMF | 2 | rt | 120 | 1150 | 97 |
| BOCCENLtBu | CO | 3,4-(OPMB)₂—PH | PMB | SO | Cl→Br | 780 | 715/1.5 | NaBr | 206/2 | An | 8 | rt | 1440 | 1110 | 85 |

TABLE 4

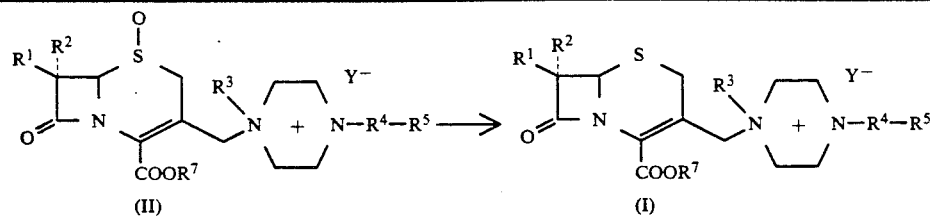

(II) → (I)

$R^2$ = H, $R^3$ = Me

[Procedure] Sulfoxide and Reducing reagent are stirred in Solvent at indicated Temp and Time.
The reaction mixture is diluted with water, filtered to remove solid, washed water, and dried to give Product (I).

| Sulfoxide (II) | | | | | | Reducing reagent | Solvent | Temp | Time | Product Crop Yield | |
|---|---|---|---|---|---|---|---|---|---|---|---|
| $R^1$ | $R^4$ | $R^5$ | $R^7$ | Y | mg | g/Eq. | ml | °C. | min. | mg | % |
| *Reduction of Sulfoxide (1)* | | | | | | | | | | | |
| G | CO | 3,4-(OPMB)$_2$—PH | PMB | I | 3150 | KI 3.42/7 + AcCl 1.28 ml/6 | An 30 | −33~−27 | 120 | 3160 | 99 |
| BOCCTX | CO | 3,4-(OPMB)$_2$—PH | PMB | I | 1165 | PCl$_3$ 2.36/18 | DMA 1.5; DCM 15 | −50~−30 | 30 | 1080 | 94 |
| BOCCTX | CH$_2$ | 3,4-(OPMB)$_2$—PH | PMB | I | 1780 | PCl$_3$ 4.72/23.5 | DMA 3; DCM 30 | −50~−30 | 180 | 1070 | 61 |
| BOCCTX | COCH$_2$ | 3,4-(OAc)$_2$—PH | PMB | I | 2000 | PCl$_3$ 4.72/19 | DMA 3; DCM 30 | −50~−30 | 30 | 1456 | 71 |
| BOCCAZtBu | CO | 3,4-(OPMB)$_2$—PH | PMB | I | 24560 | KI 29880/10 + AcCl 7.68 ml/6 | An 500 | −30~−15 | 90 | 22570 | 93 |
| BOCCAZtBu | CO | 3,4-(OAc)$_2$-2-Cl—PH | PMB | I | 120000 | KI 120/10 + AcCl 45.5 ml/6 | An 720 | 0~2 | 105 | 112400 | 95 |
| BOCCAZtBu | CO | 3,4-(OPMB)$_2$-2-Cl—PH | PMB | I | 900 | KI 1.06/11 + AcCl 0.3 ml/6 | An 10 | −30~−15 | 30 | 750 | 85 |
| BOCCAZtBu | CO | 3,4-(OPMB)$_2$-5-Cl—PH | PMB | Cl | 1367 | PCl$_3$ 3.15/22 | DMA 2; DCM 20 | −50~−25 | 60 | 1020 | 76 |
| *Reduction of Sulfoxide (2)* | | | | | | | | | | | |
| BOCCAZtBu | CO | 3,4-(OPMB)$_2$-6-Cl—PH | PMB | I | 162000 | KI 193/10 + AcCl 54.6 ml/6 | An 1130 | 0 | 90 | 155000 | 97 |
| BOCCAZtBu | CO | 3,4-(OPMB)$_2$-2,5-Cl$_2$PH | PMB | I | 780 | PCl$_3$ 1.89/23 | DMA 1.2; DCM 12 | −54~−30 | 240 | 660 | 86 |
| BOCCAZtBu | CO | 4-OPMB-3-MeO—PH | PMB | I | 2480 | PCl$_3$ 3/17 | DMA 3; DCM 25 | −50~−30 | 30 | 2280 | 93 |
| BOCCAZtBu | CH$_2$ | 3,4-(OPMB)$_2$—PH | PMB | I | 2070 | PCl$_3$ 4.72/22.5 | DMA 3.5; DCM 35 | −50~−30 | 150 | 1900 | 93 |
| BOCCAZtBu | CO | 3,4,5-(OPMB)$_3$—PH | PMB | I | 3750 | KI 6.23/15 + AcCl 1.60 ml/9 | An 38 | −30~−10 | 240 | 3410 | 92 |
| BOCCAZBH | CO | 3,4-(OPMB)$_2$—PH | PMB | I | 1150 | PCl$_3$ 3.15/29 | DMA 2; DCM 10 | −50~−30 | 60 | 908 | 80 |
| BOCENLtBu | CO | 3,4-(OPMB)$_2$—PH | PMB | Br | 1110 | KI 1.41/10 + AcCl 0.3 ml/5 | An 15 | −40~−10 | 180 | 1060 | 95 |

TABLE 5

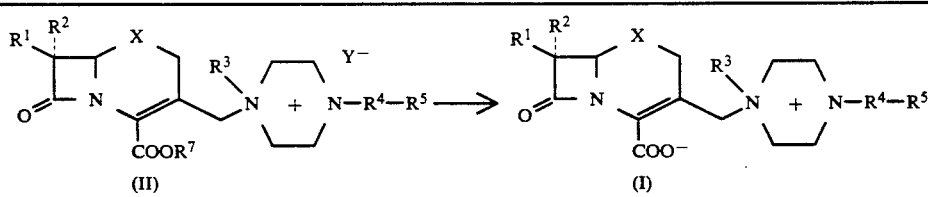

(II) → (I)

$R^2$ = H, $R^3$ = Me. BOC, tBu, PMB, & BH are deprotected too.

[Procedure] To Protected compound (II) in Solvent is added Deprotectg. agent, and the mixture is stirred at Temp for Time as given.
The reaction mixture is diluted with aq. acid, washed with organic solvent and purified by copolymer adsorbent column (aq. methanol) to give Product (I).

| Protected compound (II) | | | | | | | Deprotectg. agent mg/Eq. | Solvent ml | Temp. °C. | Time min | Product Crop Yield | |
|---|---|---|---|---|---|---|---|---|---|---|---|---|
| $R^1$ | $R^4$ | $R^5$ | $R^7$ | X | Y | mg | | | | | mg | % |
| *Deprotection (1)* | | | | | | | | | | | | |
| FMX | CO | 3,4-(OPMB)$_2$—PH | BH | MO | I | 1680 | TFA 10 ml | DCM 10; Ani 3 | 0 | 15 | 600 | 68 |
| G | CO | 3,4-(OPMB)$_2$—PH | PMB | S | I | 800 | TFA 4 ml | Ani 2.5 | 0 | 25 | 205 | 50 |
| BOCCTX | CO | 3,4-(OPMB)$_2$—PH | PMB | S | I | 1080 | AlCl$_3$ 1410/12 | DCM 10; Ani 10 | −40~−30 | 60 | 337 | 60 |
| BOCCTX | CO | 5-OPMB-4-pyridone-2- | PMB | SO | I | 140 | AlCl$_3$ 201/12 | DCM 3; Ani 1 | −40~−30 | 30 | 75 | 92 |

TABLE 5-continued

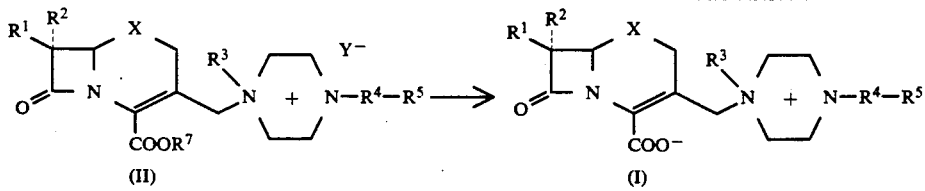

$R^2 = H$, $R^3 =$ Me. BOC, tBu, PMB, & BH are deprotected too.
[Procedure] To Protected compound (II) in Solvent is added Deprotectg. agent, and the mixture is stirred at Temp for Time as given. The reaction mixture is diluted with aq. acid, washed with organic solvent and purified by copolymer adsorbent column (aq. methanol) to give Product (I).

| | Protected compound (II) | | | | | | Deprotectg. agent mg/Eq. | Solvent ml | Temp. °C. | Time min | Product Crop Yield | |
|---|---|---|---|---|---|---|---|---|---|---|---|---|
| $R^1$ | $R^4$ | $R^5$ | $R^7$ | X | Y | mg | | | | | mg | % |
| BOCCTX | CO | 5-OPMB-4-pyridone-2- | PMB | S | I | 65 | AlCl$_3$ 95/12 | DCM 2; Ani 0.5 | −40~−30 | 30 | 10 | 27 |
| BOCCTX | COCH$_2$ | 3,4-(OAc)$_2$—PH | PMB | S | Cl | 1456 | AlCl$_3$ 1050/6 | DCM 10; Ani 10 | −40~−30 | 60 | 337 | 38 |
| BOCCTX | CH$_2$ | 3,4-(OPMB)$_2$—PH | PMB | S | I | 1070 | AlCl$_3$ 1180/10 | MeNO$_2$ 5; Ani 9 | −35 | 30 | 110 | 20 |
| BOCCAZtBu | CO | 3,4-(OPMB)$_2$—PH | PMB | S | I | 16180 | AlCl$_3$ 24000/15 | DCM 200; Ani 240 | −40 | 60 | 5240 | 62 |
| | | | | Deprotection (2) | | | | | | | | |
| BOCCAZtBu | CO | 3,4-(OPMB)$_2$-2-Cl—PH | PMB | S | I | 745 | AlCl$_3$ 1080/15 | DCM 10; Ani 10 | −40~−25 | 30 | 280 | 70 |
| BOCCAZtBu | CO | 3,4-(OPMB)$_2$-2-Cl—PH | PMB | SO | I | 420 | AlCl$_3$ 600/15 | DCM 5; Ani 4 | −40~−25 | 30 | 130 | 57 |
| BOCCAZtBu | CO | 3,4-(OPMB)$_2$-5-Cl—PH | PMB | S | Cl | 1020 | AlCl$_3$ 1580/15 | DCM 10; Ani 5 | −40~−30 | 30 | 220 | 38 |
| BOCCAZtBu | CO | 3,4-(OPMB)$_2$-6-Cl—PH | PMB | S | I | 15500 | AlCl$_3$ 22400/15 | DCM 160; Ani 80 | −40~−30 | 60 | 5100 | 62 |
| BOCCAZtBu | CO | 3,4-(OPMB)$_2$-2,5-Cl$_2$PH | PMB | S | I | 650 | AlCl$_3$ 805/13 | MeNO$_2$ 2; Ani 8 | −35 | 30 | 122 | 31 |
| BOCCAZtBu | CO | 4-OPMB-3-MeO—PH | PMB | S | I | 2280 | AlCl$_3$ 2930/12 | DCM 22; Ani 15 | −40~−30 | 30 | 345 | 26 |
| BOCCAZtBu | CH$_2$ | 3,4-(OPMB)$_2$—PH | PMB | S | I | 1900 | AlCl$_3$ 2270/12 | MeNO$_2$ 6; Ani 20 | −40~−30 | 30 | 442 | 43 |
| BOCCAZtBu | CO | 3,4,5-(OPMB)$_3$—PH | PMB | S | I | 3150 | AlCl$_3$ 5100/18 | DCM 20; Ani 20 | −40~−20 | 60 | 863 | 57 |
| BOCCAZBH | CO | 3,4-(OPMB)$_2$—PH | PMB | S | I | 900 | AlCl$_3$ 1230/15 | MeNO$_2$ 5; DCM 5; Ani 8 | −40~−30 | 30 | 220 | 51 |
| BOCENLtBu | CO | 3,4-(OPMB)$_2$—PH | PMB | S | Br | 1060 | AlCl$_3$ 1640/15 | DCM 8; Ani 18 | −40~−30 | 180 | 220 | 39 |

What we claim is:

1. A piperaziniocephalosporin of the following formula:

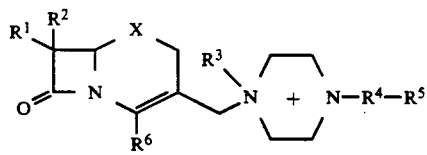

wherein,
$R^1$ is acylamino having up to 20 carbon atoms;
$R^2$ is hydrogen or methoxy;
$R^3$ is alkyl;
$R^4$ is carbonyl;
$R^5$ is substituted or unsubstituted hydroxyphenyl or hydroxypyridone, wherein said groups may be substituted by amino, hydroxy, alkali metaloxy, alkaline earth metal oxy, 1C to 8C alkoxy, 1C to 8C acyloxy, 3C to 9C silyloxy, 7C to 15C aralkoxy, 2C to 9C alkoxycarbonyloxy, halogen, nitro, cyano, carboxy, carbamoyl, 2C to 9C alkoxycarbonyl, 8C to 15C aralkoxycarbonyl, 1C to 8C alkyl, 2C to 9C alkenyl and monocyclic heterocyclyl thio;
$R^6$ has a negative charge and is COO—, or $R^6$ is an anion in combination with an unprotected or protected carboxy group, wherein said carboxy group may be protected by 1C to 8C alkyl, 7C to 19C aralkyl, 6C to 12C aryl, 1C to 12C N-substituted amino, 3C to 12C hydrocarbylsilyl and 3C to 12C hydrocarbylstannyl, or wherein said carboxy group may form an amminio, arylinio, lithium, sodium, potassium, magnesium, calcium or aluminum salt, or wherein said carboxyl group may form an ester with a moiety selected from the group consisting of:
2C to 15C alkanoyloxyalkyl,
3C to 15C alkoxycarbonyloxyalkyl, 2C to 8C alkoxyalkyl,
4C to 8C oxacyloalkyl, 8C to 12C substituted aralkyl, 6C to 12C aryl and 2C to 12C alkenyl; and
X is S or S→O.

2. A piperaziniocephalosporin of the following formula:

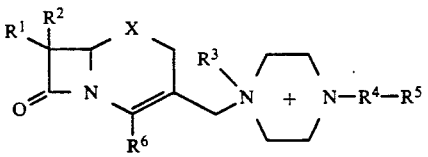

wherein,
R¹ is amino;
R² is hydrogen or methoxy;
R³ is alkyl;
R⁴ is carbonyl;
R⁵ is substituted or unsubstituted hydroxyphenyl or hydroxypyridone, wherein said groups may be substituted by amino, hydroxy, alkali metaloxy, alkaline earth metal oxy, 1C to 8C alkoxy, 1C to 8C acyloxy, 3C to 9C silyloxy, 7C to 15C aralkoxy, 2C to 9C alkoxycarbonyloxy, halogen, nitro, cyano, carboxy, carbamoyl, 2C to 9C alkoxycarbonyl, 8C to 15C aralkoxycarbonyl, 1C to 8C alkyl, 2C to 9C alkenyl and monocyclic heterocyclyl thio;
R⁶ has a negative charge and is COO⁻, or R⁶ is an anion in combination with an unprotected or protected carboxy group, wherein said carboxy group may be protected by 1C to 8C alkyl, 7C to 19C aralkyl, 6C to 12C aryl, 1C to 12C N-substituted amino, 3C to 12C hydrocarbylsilyl and 3C to 12C hydrocarbylstannyl, or wherein said carboxy group may form an amminio, arylinio, lithium, sodium, potassium, magnesium, calcium or aluminum salt, or wherein said carboxyl group may form an ester with a moiety selected from the group consisting of:
2C to 15C alkanoyloxyalkyl,
3C to 15C alkoxycarbonyloxyalkyl, 2C to 8C alkoxyalkyl,
4C to 8C oxacyloalkyl, 8C to 12C substituted aralkyl, 6C to 12C aryl and 2C to 12C alkenyl; and
X is S or S→O.

3. A method for combatting bacteria which comprises bringing an effective amount of a piperaziniocephalosporin as claimed in claim 2 into contact with the bacteria.

4. A method for combatting bacteria as recited in claim 3, wherein the bacteria is selected from the group consisting of:
*Pseudomonas aeruginosa, Serrati marcescens, Morgania morganii, Enterobacter cloacae* and *Clostridium freundii.*

5. An antibacterial composition comprising an effective amount of piperaziniocephalosporin as claimed in claim 2 and a pharmaceutical carrier.

6. A compound selected from the group consisting of:
7β-phenylacetamido-3-[4-(3-,4-dihydroxybenzoyl)-1-methylpiperazinio]methyl-3-cephem-4-carboxylic acid and its 1-oxide,
7β-difluoromethylthioacetamido-3-[4-(3,4-dihydroxybenzoyl)-1-methylpiperazinio]methyl-3-cephem-4-carboxylic acid and its 1-oxide,
7β-[2-(2-aminothiazol-4-yl)-2-methoxyiminoacetamido-3-[4-(3,4-dihydroxybenzoyl)-1-methylpiperazinio]-methyl-3-cephem-4-carboxylic acid and its 1-oxide,
7β-[2-(2-aminothiazol-4-yl)-2-methoxyiminoacetamido-3-[4-(5-hydroxy-4-pyridone-2-ylcarbonyl)-1-methylpiperazinio]methyl-3-cephem-4-carboxylic acid and its 1-oxide,
7β-[2-(2-aminothiazol-4-yl)-2-methoxyiminoacetamido-3-[4-(3,4-hydroxyphenylacetyl)-1-methylpiperazinio]methyl-3-cephem-4-carboxylic acid and its 1-oxide,
7β-[21-(2-aminothiazol-4-yl)-2-methoxyiminoacetamido-3-[4-(3,4-dihydroxybenzyl)-1-methylpiperazinio]methyl-3-cephem-4-carboxylic acid and its 1-oxide,
7β-[2-(2-aminothiazol-4-yl)-2-(1-carboxy-1-methylethoxyimino)acetamido-3-[4-(3,4-dihydroxybenzoyl)-1-methylpiperazinio]methyl-3-cephem-4-carboxylic acid and its 1-oxide,
7β-[2-(2-aminothiazol-4-yl)-2-(1-carboxy-1-methylethoxyimino)acetamido-3-[4-(2-chloro-3,4-dihydroxybenzoyl)-1-methylpiperazino]-methyl-3-cephem-4-carboxylic acid and its 1-oxide,
7β-[2-(2-aminothiazol-4-yl)-2-(1-carboxy-1-methylethoxyimino)acetamido-3-[4-(5-chloro-3,4-dihydroxybenzoyl)-1-methylpiperazino]-methyl-3-cephem-4-carboxylic acid and its 1-oxide,
7β-[1-(2-aminothiazol-4-yl)-2-(1-carboxy-1-methylethoxyimino)acetamido-3-[4-(6-chloro-3,4-dihydroxybenzoyl)-1-methylpiperazino]-methyl-3-cephem-4-carboxylic acid and its 1-oxide,
7β-[1-(2-aminothiazol-4-yl)-2-(1-carboxy-1-methylethoxyimino)acetamido-3-[4-(2,5-dichloro-3,4-dihydroxybenzoyl)-1-methylpiperazino]-methyl-3-cephem-4-carboxylic acid and its 1-oxide,
7β-[1-(2-aminothiazol-4-yl)-2-(1-carboxy-1-methylethoxyimino)acetamido-3-[4-(3-methoxy-4-hydroxybenzoyl)-1-methylpiperazinio]methyl-3-cephem-4-carboxylic acid and its 1-oxide,
7β-[1-(2-aminothiazol-4-yl)-2-(1-carboxy-1-methylethoxyimino)acetamido-3-[4-(3,4-dihydroxybenzyl)-1-methylpiperazinio]methyl-3-cephem-4-carboxylic acid and its 1-oxide,
7β-[1-(2-aminothiazol-4-yl)-2-(1-carboxy-1-methylethoxyimino)acetamido-3-[4-(3,4,5-trihydroxybenzyl)-1-methylpiperazinio]methyl-3-cephem-4-carboxylic acid and its 1-oxide,
7β-[1-(2-aminothiazol-4-yl)-2-(1-carboxy-1-methylethoxyimino)acetamido-3-[4-(3,4-dihydroxyenzoyl)-1-methylpiperazinio]-methyl-3-cephem-4-carboxylic acid and its 1-oxide;
and protected derivatives thereof.

7. A compound as claimed in claim 1 wherein R¹ is 2-(2-amino-4-thiazolyl)-2-alkoxyiminoacetamido or 2-(2-amino-4-thiazolyl)-2-carboxyalkoxyiminoacetamido.

8. A compound as claimed in claim 1 or 2 wherein R² is hydrogen.

9. A compound as claimed in claim 1 or 2 wherein R³ is methyl.

10. A compound as claimed in claim 1 or 2 wherein R⁴ is carbonyl or methylene.

11. A compound as claimed in claim 1 or 2 wherein R⁵ is protected or unprotected hydroxyphenyl which is unsubstituted or substituted by amino hydroxy, protected hydroxy, halogen, nitro, cyano, carboxy, carbamoyl, alkoxycarbonyl, aralkoxycarbonyl, alkyl, alkenyl or arylthio.

12. A compound as claimed in claim 1 or 2, wherein R⁵ is a 3,4-dihydroxyphenyl moiety, which is unsubstituted or substituted by chlorine.

13. A compound as claimed in claim 1 or 2, wherein R⁵ is a substituted or unsubstituted vicinal dihydroxyphenyl moiety or a substituted or unsubstituted vicinal dihydroxy pyridyl moiety, either of which moieties may be substituted by methyl, chloro, or alkoxy.

14. A compound as claimed in claim 1 or 2 wherein $R^6$ is $COO^-$.

15. A method for combating bacteria which comprises bringing an effective amount of a piperaziniocephalosporin as claimed in claim 1 or 2 into contact with the bacteria.

16. An antibacterial composition comprising an effective amount of a piperaziniocephalosporin as claimed in claim 1 or 2 and a pharmaceutical carrier.

17. A method for combating bacteria which comprises bringing an effective amount of a piperaziniocephalosporin as claimed in claim 1 into contact with the bacteria.

18. A method for combatting bacteria as recited in claim 17, wherein the bacteria is selected from the group consisting of:

Pseudomonas aeruginosa, Serrati marcescens, Morgania morganii, Enterobacter cloacae and Clostridium freundii.

19. An antibacterial composition comprising an effective amount of a piperaziniocephalosporin as claimed in claim 1 and a pharmaceutical carrier.

* * * * *